(12) United States Patent
Zhang et al.

(10) Patent No.: US 9,504,394 B2
(45) Date of Patent: Nov. 29, 2016

(54) ELECTRO-OPTICAL SYSTEM, APPARATUS, AND METHOD FOR AMBULATORY MONITORING

(75) Inventors: Quan Zhang, Winchester, MA (US); Gary Strangman, Tewksbury, MA (US)

(73) Assignee: The General Hospital Corporation, Boston, MA (US)

( * ) Notice: Subject to any disclaimer, the term of this patent is extended or adjusted under 35 U.S.C. 154(b) by 1990 days.

(21) Appl. No.: 11/995,352

(22) PCT Filed: Jul. 12, 2006

(86) PCT No.: PCT/US2006/026963
§ 371 (c)(1),
(2), (4) Date: Jan. 11, 2008

(87) PCT Pub. No.: WO2007/018921
PCT Pub. Date: Feb. 15, 2007

(65) Prior Publication Data
US 2008/0208013 A1 Aug. 28, 2008

Related U.S. Application Data

(60) Provisional application No. 60/703,173, filed on Jul. 28, 2005.

(51) Int. Cl.
| | |
|---|---|
| G01N 33/48 | (2006.01) |
| G01N 33/50 | (2006.01) |
| A61B 5/024 | (2006.01) |
| A61B 5/00 | (2006.01) |
| A61B 5/1455 | (2006.01) |
| G06F 19/26 | (2011.01) |
| G06F 19/12 | (2011.01) |

(52) U.S. Cl.
CPC ......... *A61B 5/02438* (2013.01); *A61B 5/0002* (2013.01); *A61B 5/0059* (2013.01); *A61B 5/1455* (2013.01); *A61B 5/4094* (2013.01); *A61B 5/4509* (2013.01); *A61B 5/7232* (2013.01); *G06F 19/12* (2013.01); *G06F 19/26* (2013.01)

(58) Field of Classification Search
None
See application file for complete search history.

(56) References Cited

U.S. PATENT DOCUMENTS

| | | |
|---|---|---|
| 5,167,230 A | 12/1992 | Chance |
| 5,507,288 A | 4/1996 | Böcker et al. |
| 5,514,079 A * | 5/1996 | Dillon ............................ 601/151 |
| 5,692,520 A * | 12/1997 | Lavoisier ..................... 600/587 |
| 5,779,631 A | 7/1998 | Chance |
| 5,873,821 A | 2/1999 | Chance et al. |
| 6,397,099 B1 | 5/2002 | Chance |

(Continued)

FOREIGN PATENT DOCUMENTS

| | | |
|---|---|---|
| EP | 0 682 727 A1 | 11/1995 |
| WO | WO 01/82099 A1 * | 11/2001 |

OTHER PUBLICATIONS

Han et al. Quantum-dot-tagged microbeads for multiplexed optical coding of biomolecules. Nature Biotechnology, 2001, vol. 19, pp. 631-635.*

(Continued)

*Primary Examiner* — Russell S Negin
(74) *Attorney, Agent, or Firm* — Quarles & Brady LLP

(57) ABSTRACT

An electro-optical system, apparatus, and method allow long-term, ambulatory measurements to be made on a patient using light transmitted into the patient and resulting light received from the patient.

37 Claims, 9 Drawing Sheets

(56) References Cited

U.S. PATENT DOCUMENTS

| | | |
|---|---|---|
| 6,402,689 B1 | 6/2002 | Scarantino et al. |
| 6,527,729 B1 * | 3/2003 | Turcott ............... 600/528 |
| 6,549,795 B1 | 4/2003 | Chance |
| 6,785,568 B2 | 8/2004 | Chance |
| 6,790,178 B1 | 9/2004 | Mault et al. |
| 2002/0054134 A1 * | 5/2002 | Kelts ............... 345/788 |
| 2002/0161291 A1 | 10/2002 | Kianl et al. |
| 2005/0113656 A1 | 5/2005 | Chance |

OTHER PUBLICATIONS

Chance et al. Phase measurement of light absorption and scatter in human tissue. Review of Scientific Instruments, vol. 69, 1998, pp. 3457-3481.*

Chen et al. Correlation between near-infrared spectroscopy and magnetic resonance imaging of rat brain oxygenation modulation. Physics in Medicine and Biology, vol. 48, 2003, pp. 417-427.*

Zhang et al.; "Study of Near Infrared Technology for Intracranial Hematoma Detection;" Journal of Biomedical Optics; vol. 5, No. 2; Apr. 2000; 206-213.

PCT Search Report and Written Opinion of the ISA for PCT/US2006/026963, filed on Jul. 12, 2006.

Picard et al.; "Affective Wearables;" First International Symposium on Wearable Computers, 1997 Digest of Papers; ISBN: 0/8186/8192/6; Oct. 13-14, 1997; pp. 90-97.

Hoshi; "Functional near-infrared optical imaging: Utility and limitations in human brain mapping;" Psychophysiology, vol. 40, Issue 4; 2003; Jun. 10, 2003; pp. 511-520.

Hoshi et al.; "Regional Cerebral Blood Flow Changes Associated With Emotions in Children;" Pediatric Neurology, vol. 27, Issue 4; Oct. 2002; pp. 275-281.

Shiga et al.; Study of an Algorithm Based on Model Experiments and Diffusion Theory for a Portable Tissue Oximeter; Journal of Biomedical Optics, vol. 2, No. 2, Apr. 1997; pp. 154-161.

Zhang et al.; "Study of near infrared technology for intracranial hematoma detection;" Journal of Biomedical Optics, vol. 5, No. 2; Apr. 2000; pp. 206-213.

* cited by examiner

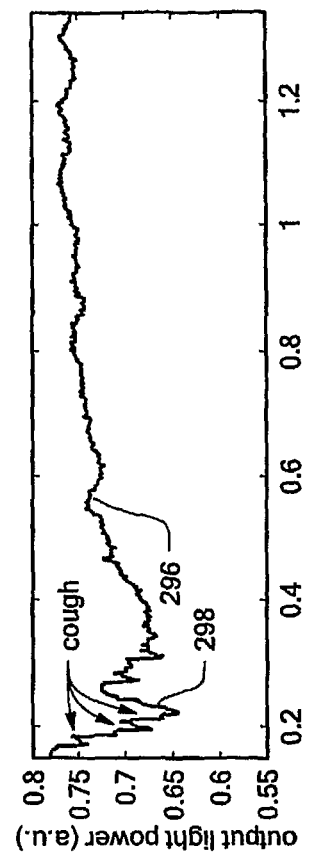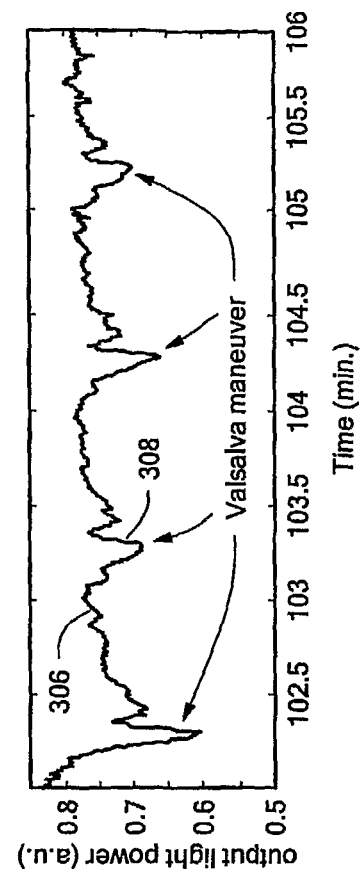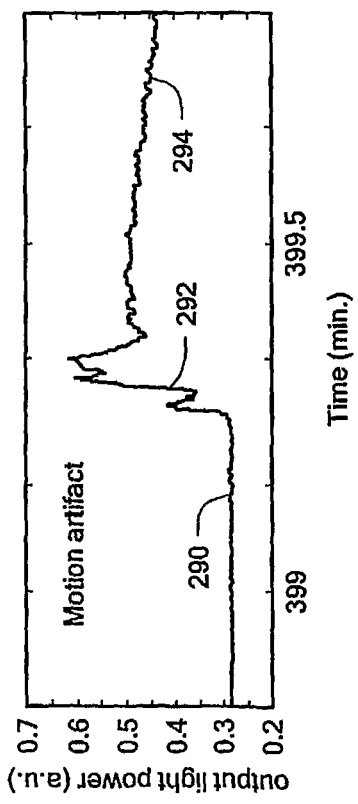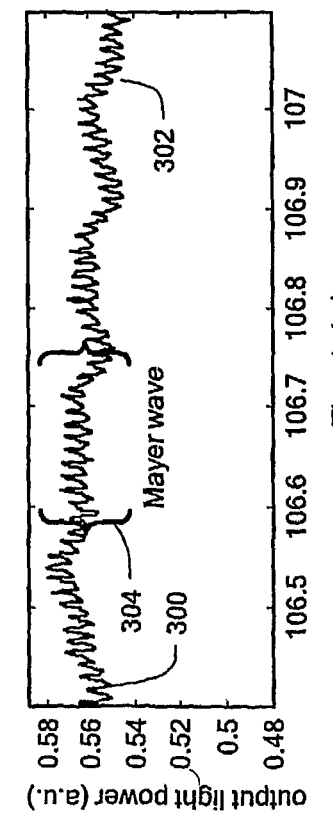
FIG. 6A
FIG. 6C
FIG. 6
FIG. 6B

ELECTRO-OPTICAL SYSTEM, APPARATUS, AND METHOD FOR AMBULATORY MONITORING

CROSS REFERENCE TO RELATED APPLICATIONS

This application is a U.S. National Stage application under 35 U.S.C. §371 and claims the benefit of PCT Patent Application No. PCT/US2006/026963, entitled "ELECTRO-OPTICAL SYSTEM, APPARATUS, AND METHOD FOR AMBULATORY MONITORING," filed on Jul. 12, 2006, which application claims the benefit of U.S. Provisional Application No. 60/703,173, filed Jul. 28, 2005, both of which are incorporated by reference herein in their entirety.

GOVERNMENT LICENSE RIGHTS

This invention was made with government support under NCC 9-58 awarded by the National Aeronautics and Space Administration and R21-EB002416 awarded by the National Institutes of Health. The government has certain rights in the invention.

FIELD OF THE INVENTION

This invention relates generally to electro-optical systems, apparatus, and methods and, more particularly, to an electro-optical system, apparatus, and method that can be used under ambulatory conditions.

BACKGROUND OF THE INVENTION

As is known, a so-called "Holter" monitor allows ambulatory EKG measurement of a patient. A Holter monitor generates an electrocardiogram (EKG) recording over a period of 24 or more hours. Three electrodes are attached to the patient's chest and connected to a small portable EKG recorder by lead wires. When operating, the patient goes about his or her usual daily activities (except for activities such as taking a shower, swimming, or any activity causing an excessive amount of sweating which would cause the electrodes to become loose or fall off).

There are two conventional types of Holter monitoring. For continuous recording, the EKG is recorded continuously during the entire testing period. For event monitoring, or loop recording, the EKG is recorded only when the patient starts the recording, i.e., when symptoms are felt. The patient starts the event monitoring by pushing a button or the like.

Holter monitoring may be done when a heart arrhythmia is suspected but not seen on a resting or signal-average EKG, since arrhythmias may be transient or intermittent and may not be seen during the shorter recording times of the resting or signal-average EKG.

While the Holter monitor allows an EKG trace to be generated in an ambulatory environment, e.g., during usual daily activities, the EKG is only useful to diagnose certain medical conditions. A variety of other medical conditions may also be intermittent in nature. For example, a dizzy spell, or hot flashes can occur intermittently. The Holter monitor, which provides an EKG, is not well suited to detect and to characterize these or some other types of intermittent medical conditions. For these, different ambulatory monitors are more appropriate.

Apparatus and techniques are known which transmit light into a patient and receive resulting light from the patient. One such apparatus, a pulse oximeter, transmits light into a finger of a patient and uses the resulting received light to determine a blood oxygenation level of the patient. Other, more complex systems under exploration and development, use multiple light sources and multiple light receivers to detect such medical conditions as hemorrhage and ischemia.

Existing apparatus, which generates light into and receives light from a patient, is known to be bulky and not suitable for ambulatory measurements. Some such apparatus requires that bulky light fibers be attached to the patient.

SUMMARY OF THE INVENTION

In accordance with the present invention, an electro-optical monitoring system includes a light transceiver adapted to transmit light into biological tissue of a person at a light transmission rate of at least 0.1 light transmissions per second, and to receive light from the biological tissue resulting from the transmitted light, and to provide a transceiver output signal indicative of a characteristic of the received light. The electro-optical monitoring system further includes a signal processor coupled to the light transceiver and adapted to process the transceiver output signal to provide a processed signal. The processed signal includes signal samples having a sample rate of at least 0.1 samples per second. The electro-optical monitoring system still further includes a storage device coupled to the signal processor and adapted to store at least four hours of the processed signal as a stored-processed signal, wherein the stored-processed signal has a stored signal duration sufficient to detect an intermittent medical condition of the person having an occurrence period of at least four hours. In some embodiments, the electro-optical monitoring system can still further include an external computing platform for data analysis.

In accordance with another aspect of the present invention, an electro-optical monitoring system includes a light transceiver adapted to transmit light transceiver into biological tissue of a person, to receive light from the biological tissue resulting from the transmitted light, and to provide a transceiver output signal indicative of a characteristic of the received light. The electro-optical monitoring system further includes a signal processor coupled to the light transceiver and adapted to process the transceiver output signal to provide a processed signal. The electro-optical monitoring system still further includes a storage device coupled to the signal processor and adapted to store the processed signal as a stored-processed signal. The storage device includes a recirculating buffer memory coupled to the signal processor and a capture memory coupled to the recirculating buffer memory. Contents of the recirculating buffer memory are transferred to the capture memory in response to at least one of an event detection by the signal processor or a manual indication. In some embodiments, the electro-optical monitoring system can still further include an external computing platform for data analysis.

In accordance with yet another aspect of the present invention, an electro-optical monitoring system includes a light transceiver adapted to transmit light into biological tissue of a person, to receive light from the biological tissue resulting from the transmitted light, and to provide a transceiver output signal indicative of a characteristic of the received light. The electro-optical monitoring system further includes an event input device adapted to receive a manual indication that a symptom associated with a medical condition is occurring. In one embodiment, a user manually activates the event input device at a time when a symptom of interest is occurring. Thus, in this case, the event input device is a manual device. The event input device provides an event signal indicative of the manual indication. The electro-optical monitoring system still further includes a signal processor coupled to the light transceiver. The signal processor is adapted to process the transceiver output signal and the event signal to provide a processed signal. The electro-optical monitoring system still further includes a storage device coupled to the signal processor. The storage device is adapted to store the processed signal as a stored-processed signal. In some embodiments, the electro-optical monitoring system can still further include an external computing platform for data analysis.

In accordance with yet another aspect of the present invention, an electro-optical monitoring system includes a light transceiver adapted to transmit light into biological tissue of a person and to receive fluorescent light from the biological tissue resulting from the transmitted light. The transmitted light and the fluorescent light are at different wavelengths. The light transceiver is further adapted to provide a transceiver output signal indicative of a characteristic of the received fluorescent light. The electro-optical monitoring system further includes a signal processor coupled to the light transceiver and adapted to process the transceiver output signal to provide a processed signal. The electro-optical monitoring system still further includes a storage device coupled to the signal processor and adapted to store the processed signal as a stored-processed signal. In some embodiments, the electro-optical monitoring system can still further include an external computing platform for data analysis.

In accordance with yet another aspect of the present invention, an electro-optical monitoring system includes a light transceiver adapted to transmit light into biological tissue of a person, to receive light from the biological tissue resulting from the transmitted light, and to provide a transceiver output signal indicative of a characteristic of the received light. The electro-optical monitoring system further includes a motion sensor disposed on the light transceiver and adapted to sense motion of at least one of the person or the transceiver and to provide a motion signal indicative of the motion. The electro-optical monitoring system still further includes a signal processor coupled to the light transceiver and adapted to process the transceiver output signal and the motions signal to provide a processed signal. The electro-optical monitoring system still further includes a storage device coupled to the signal processor and adapted to store the processed signal as a stored-processed signal. In some embodiments, the electro-optical monitoring system can still further include an external computing platform for data analysis.

In accordance with yet another aspect of the present invention, an electro-optical monitoring system includes a light transceiver adapted to transmit light into biological tissue of a person, to receive light from the biological tissue resulting from the transmitted light, and to provide a transceiver output signal indicative of a characteristic of the received light. The light transceiver has an adhesive surface such that the light transceiver can be directly adhesively coupled to the person. The electro-optical monitoring system further includes a signal processor coupled to the light transceiver and adapted to process the transceiver output signal to provide a processed signal. The electro-optical monitoring system still further includes a storage device coupled to the signal processor and adapted to store the processed signal as a stored-processed signal. In some embodiments, the electro-optical monitoring system can still further include an external computing platform for data analysis.

In accordance with yet another aspect of the present invention, an electro-optical monitoring system includes a light transceiver adapted to transmit light into biological tissue of a person, to receive light from the biological tissue resulting from the transmitted light, and to provide a transceiver output signal indicative of a characteristic of the received light. The electro-optical monitoring system further includes a modulator adapted to amplitude modulate the transmitted light, and a demodulator adapted to demodulate the transceiver output signal and to provide at least one of an amplitude signal or a phase signal. The amplitude and phase signals can be related to the absorption and scattering characteristics in the biological tissue. The electro-optical monitoring system still further includes a signal processor coupled to the demodulator and adapted to process the at least one of the amplitude signal or the phase signal to provide a processed signal. The electro-optical monitoring system still further includes a storage device coupled to the signal processor and adapted to store the processed signal as a stored-processed signal. In some embodiments, the electro-optical monitoring system can still further include an external computing platform for data analysis.

In accordance with yet another aspect of the present invention, a method of monitoring a person under ambulatory conditions includes transmitting light into the person at a light transmission rate of at least 0.1 light transmissions per second, receiving light from the person in response to the transmitting, generating a transceiver output signal indicative of a characteristic of the received light in response to the receiving, processing the transceiver output signal to provide a processed signal, wherein the processed signal includes signal samples having a sample rate of at least 0.1 samples per second. The process further includes storing at least four hours of the processed signal as a stored-processed signal, wherein the stored-processed signal has a stored signal duration sufficient to detect an intermittent medical condition of the person having an occurrence period of at least four hours.

While a variety of systems are described above, it should be appreciated that methods associated with each of the systems are also part of the invention.

BRIEF DESCRIPTION OF THE DRAWINGS

The foregoing features of the invention, as well as the invention itself may be more fully understood from the following detailed description of the drawings, in which:

FIGS. 6-6C are graphs, each showing a transceiver output signal from one embodiment of the present invention, having signals associated with the electro-optical apparatus of FIGS. 1-3 in response to particular physiological affects.

DETAILED DESCRIPTION OF THE INVENTION

Before describing the present invention, some introductory concepts and terminology are explained. As used herein, the term "transmitted light" is used to describe light transmitted from an electro-optical apparatus toward biological tissue of a person. As used herein, the term "intrinsic light" refers to transmitted light propagating within the biological tissue. As is known, intrinsic light can undergo absorption and/or scattering within biological tissue. As used herein, the term "received light" refers to intrinsic light, which exits the biological tissue, and which is received by the electro-optical apparatus.

As used herein, the term "fluorescent light" is used to describe light at a first wavelength that is emitted by a biological tissue in response to intrinsic light at a second wavelength. Therefore, the intrinsic light acts as a stimulus, which causes the emission of fluorescent light from the biological tissue. Fluorescent light can be generated by natural biological tissue. Fluorescent light can also be generated by fluorochromes, which are disposed in the biological tissue by injection, drug ingestion, or by other means.

As used herein, the phrase "ambulatory patient" refers to a patient who is mobile to a substantial extent, including, for example, mobile with or without assistance in a hospital environment, or fully mobile in an every day environment, for example, at work with or without assistance from other persons or devices.

Figure 1:
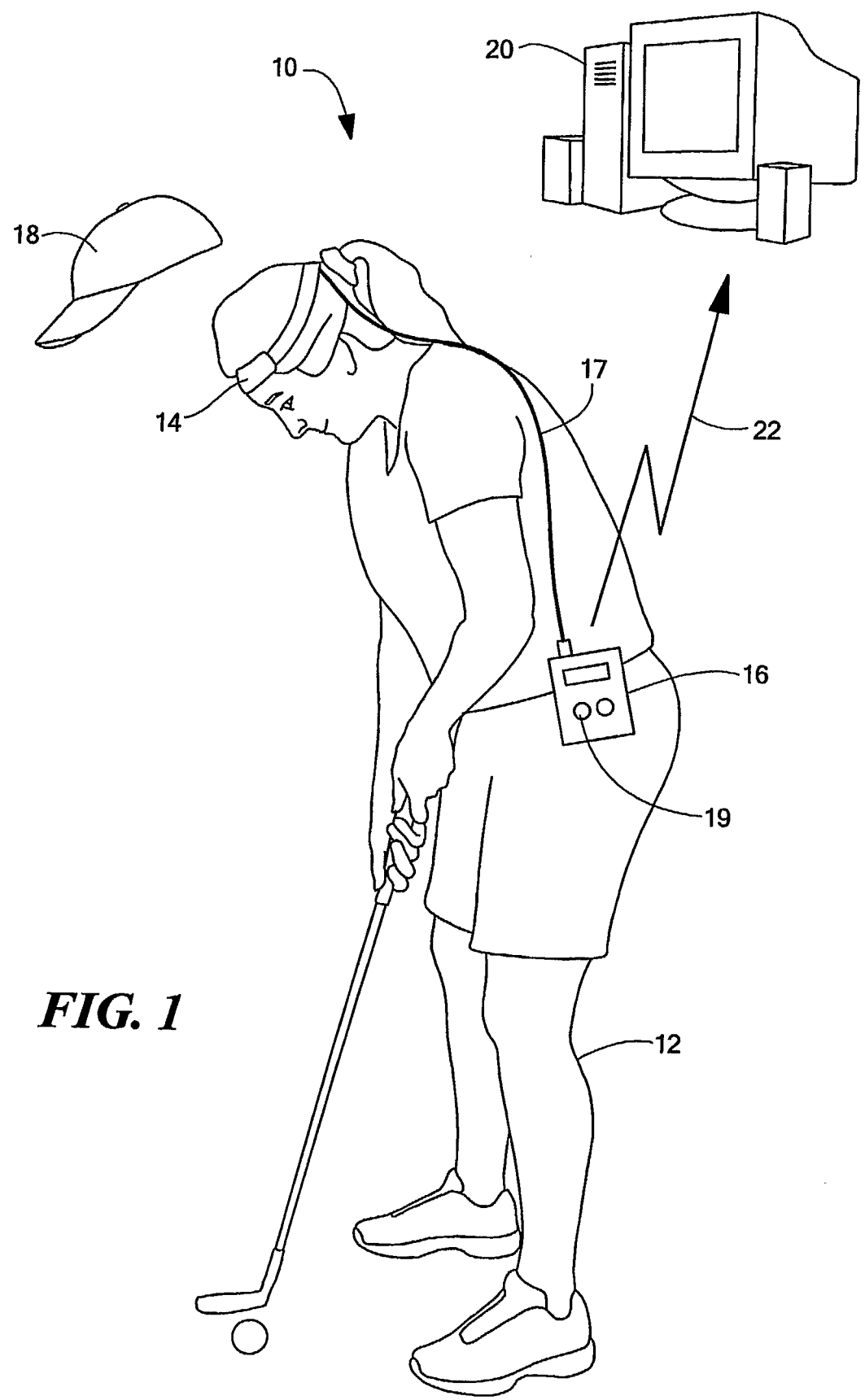
FIG. 1 is a pictorial showing a person wearing an electro-optical apparatus having a first portion including a light transceiver and a processing/storage unit.

Referring to FIG. 1, an exemplary electro-optical system 10 has elements, which are attached to a person 12. However, it will be recognized that the person 12 does not constitute an element of the system 10, but is merely shown for clarity. The system 10 includes a first portion, including a light transceiver 14 and a signal processing/storage unit 16. The light transceiver 14 is shown on the head of the person 12, but can be placed anywhere on the person 12. The signal processing/storage unit 16 can include an event input device 19, for example, a switch (e.g. a push button switch) or other element, which can be activated at a particular point in time. The signal processing/storage unit 16 is in communication with the light transceiver 14. Such communication can be facilitated, for example, via a wireless or a hard-wired signal path 17. In one embodiment, the signal path 17 can be implemented via flexible wires.

In some embodiments, the first portion 14, 16, 17 can also include a cover 18, disposed over the light transceiver 14. As will become apparent, the cover 18 can prevent stray light from entering light receivers within the light transceiver 14. In some embodiments, the cover 18 is a soft cap worn over the head.

The electro-optical system 10 can also include an external computing platform 20. The signal processing/storage unit 16 can communicate with the external computing platform 20 via a communication link 22, which can be a wireless or a wired communication link.

Operation of the electro-optical system 10 is described more fully below in conjunction with FIG. 2. However, let it suffice here to say that the light transceiver 14 is adapted to project transmitted light toward biological tissue of the person 12 (i.e., such that light impinges upon the person 12), for example, the head of the person, to receive intrinsic light exiting the biological tissue, and to provide a transceiver output signal on the signal path 17 in response to the received light. The signal processing/storage unit 16 is adapted to receive and process the transceiver output signal, to generate a processed signal, and also to store the processed signal.

In some embodiments, the signal processing/storage unit 16 is adapted to store at least four hours of the processed signal as a stored-processed signal, wherein the stored-processed signal has a stored signal duration sufficient to detect an intermittent medical condition of the person having an occurrence period of at least four hours. In other embodiments, the signal processing/storage unit 16 is adapted to store more than twenty-four hours of the processed signal as a stored-processed signal, wherein the stored-processed signal has a stored signal duration sufficient to detect an intermittent medical condition of the person having an occurrence period of at least four hours. In still other embodiments, the signal processing/storage unit 16 is adapted to store more than forty-eight hours of the processed signal as a stored-processed signal, wherein the stored-processed signal has a stored signal duration sufficient to detect an intermittent medical condition of the person having an occurrence period of at least four hours.

In some embodiments the signal processing/storage unit 16 is adapted to store signal samples having a sample rate of at least 0.1 samples per second for the above-described time periods. In other embodiments, the sample rate is higher, for example, at least two times a heartbeat rate of a person to whom the wearable light transceiver 14 is coupled. In still other embodiments, the sample rate is still higher, for example, at least ten samples per second. Furthermore, in some embodiments, the signal processing/storage unit 16 is adapted to control the light transceiver 14 to transmit light pulses into the person 12 at a predetermined light transmission rate and with a predetermined light transmission duty cycle. The light transmission rate can be determined according to the above-identified sample rates.

In some embodiments, the signal processing/storage unit 16 is adapted to receive the transceiver output signal from the light transceiver 14 and to identify one or more medical conditions, which occur under ambulatory conditions, in response to the signal. In some other embodiments, the external computing platform 20 is adapted to receive the stored-processed signal (i.e., receive a data playback) and to identify one or more medical conditions, which occur under ambulatory conditions, in response to the stored-processed signal.

It will be recognized that a variety of medical conditions can be intermittent, and therefore, difficult to detect when the patient is in a resting condition, for example, during a doctor's office visit. It will also be recognized that some intermittent medical conditions are best monitored when the person 12 is ambulatory. Because the first portion 14, 16, 17 of the system 10 is wearable under ambulatory conditions, and because, in some embodiments, the signal processing/storage unit 16 is able to store a substantial duration of the processed signal, the system 10 is suited to measure and/or to detect the intermittent medical conditions.

The above-described intermittent medical conditions include, but are not limited to, syndromes in the areas of cardiac and cerebrovascular disease (including but not limited to syncope, dysrhythmia, stroke, subdural hemorrhage), among other disorders such as epileptic seizures, vasomotor symptoms ("Hot flashes"), sudden infant death syndrome (SIDS), dizzy spells, stroke recovery, and auditory (or other) hallucination. Long term ambulatory monitoring may also be applied to reveal the pharmacokinetics and pharmacodynamics of drugs, bone density changes, and fat tissue content changes. This is achieved by optically monitoring the changes of the concentration of related molecules such as deoxyhemoglobin (HHb), oxyhemoglobin ($O_2$Hb), water, lipid; changes of tissue scattering properties, or changes in lifetime, and/or a quantum yield of a fluorochrome molecule over a certain spatial area and temporal period.

Figures 2, 3:
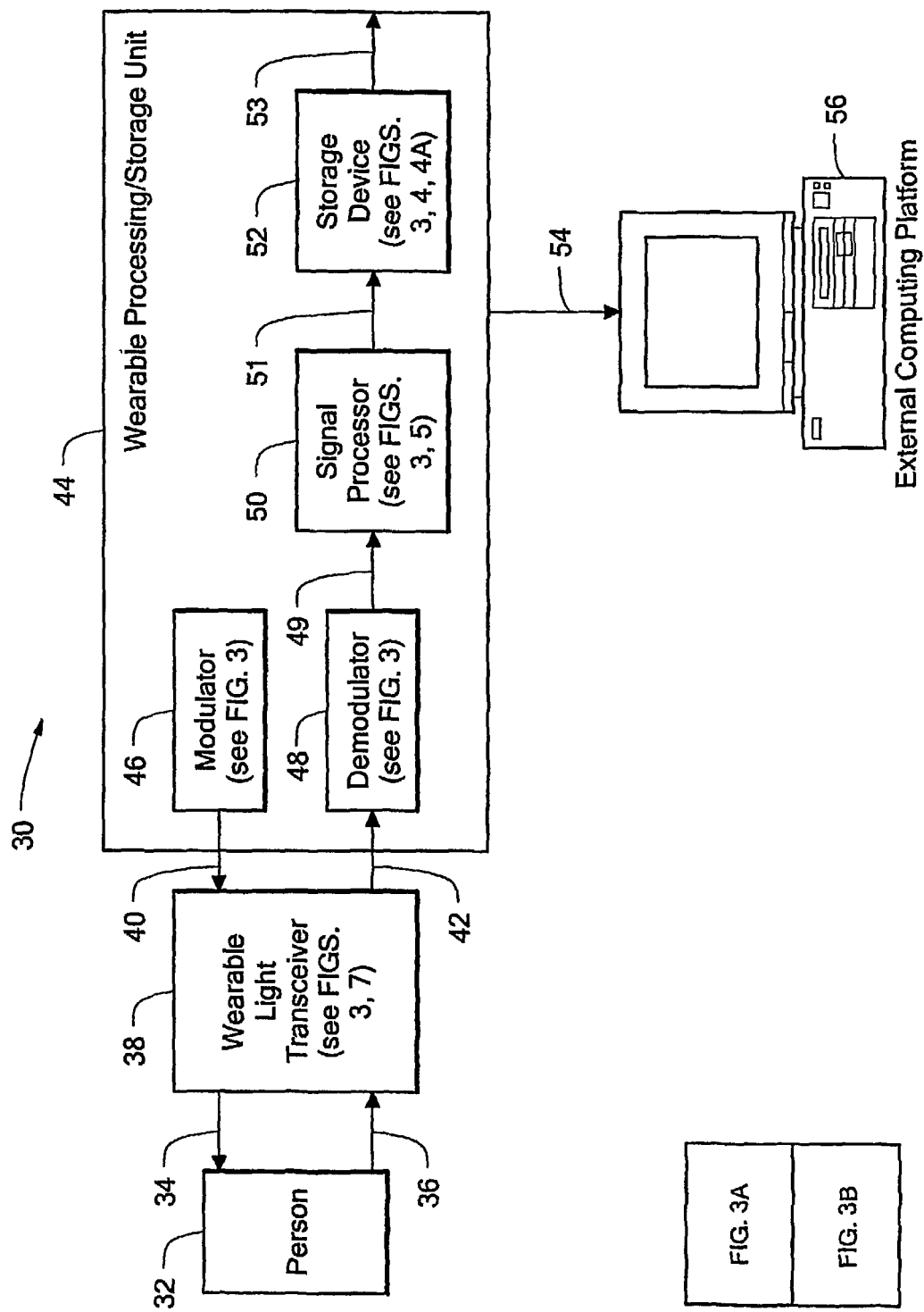
FIG. 2 is a block diagram showing further details of the first portion of FIG. 1, including the light transceiver and the processing/storage unit having a signal processor and a storage device, FIG. 3, which includes

Referring now to FIG. 2, an electro-optical system 30 can be the same as or similar to the electro-optical system 10 of FIG. 1. The system 30 includes a light transceiver 38, coupled to a processing/storage unit 44. The light transceiver 38 and processing/storage unit 44 are provided having a size, weight, shape, and design (e.g., self-contained battery) selected such that they can be worn by a user under ambulatory conditions. In some embodiments, the processing/storage unit 44 weighs less than two pounds. In some embodiments the light transceiver 38 and the processing/storage unit 44 are provided in the same physical housing or package, while in other embodiments, they are provided in different housings or packages. The processing/storage unit 44 can include a modulator 46, a demodulator 48, a signal processor 50, and a storage device 52. The processing/storage unit 44 can be coupled to an external computing platform 56 via a wireless or wired communication link (or signal path) 54.

In operation, the modulator 46 generates a modulated signal 40, which is adapted to modulate one or more light sources (not shown) included in the light transceiver 38, to generate modulated transmitted light 34, which impinges upon a person 32. Received (intrinsic) light 36 exits the biological tissue of the person 32. Since the transmitted light 34 is modulated, the received light 36 is also modulated. The light transceiver 38 receives the light 36 and in response thereto, generates a transceiver output signal 42, which is similarly modulated. The demodulator 48 demodulates the modulated transceiver output signal 42 and provides a demodulated signal 49 to the signal processor 50. The modulation/demodulation provided by the modulator 46 and the demodulator 48 are described more fully below in conjunction with FIG. 3.

The signal processor 50 processes the demodulated signal 49 to provide a processed signal 51. The processed signal 51 can be stored in the storage device 52. A stored-processed signal (data) 53 can be later retrieved from the storage device 52.

In some embodiments, the signal processor 50 performs only a small amount of processing, for example, buffering or removal of undesirable artifacts from the demodulated signal 49. In other embodiments, the signal processor 50 performs a larger amount of processing on the demodulated signal, as will become apparent from the discussion below in conjunction with FIG. 5.

It should be appreciated that the amounts of processing provided by the signal processor 50 and the external computing platform 56 can be partitioned in any way. In other words, the signal processor 50 can do all or nearly all of the signal processing associated with the electro-optical system 30 and the processing/storage unit 44 can communicate the processed signal 51 or the stored-processed signal 53 to the external computing platform 56. In other embodiments, the signal processor 50 and the external computing platform 54 perform substantially the same processing simultaneously or in series on the demodulated signal 49. In still other embodiments, all or nearly all of the processing associated with the electro-optical system 30 can be performed by the external computing platform 56, and the processing performed by the external computing platform 56 can be performed on the demodulated signal 49, and/or on the processed signal 51, and/or on the stored processed signal 53.

While a modulator 46 and a demodulator 48 are shown, in other embodiments, the transmitted light 34 is not modulated and the received light is also not modulated. In these embodiments, the modulator 46 and a demodulator 48 are not required.

Figure 3A:
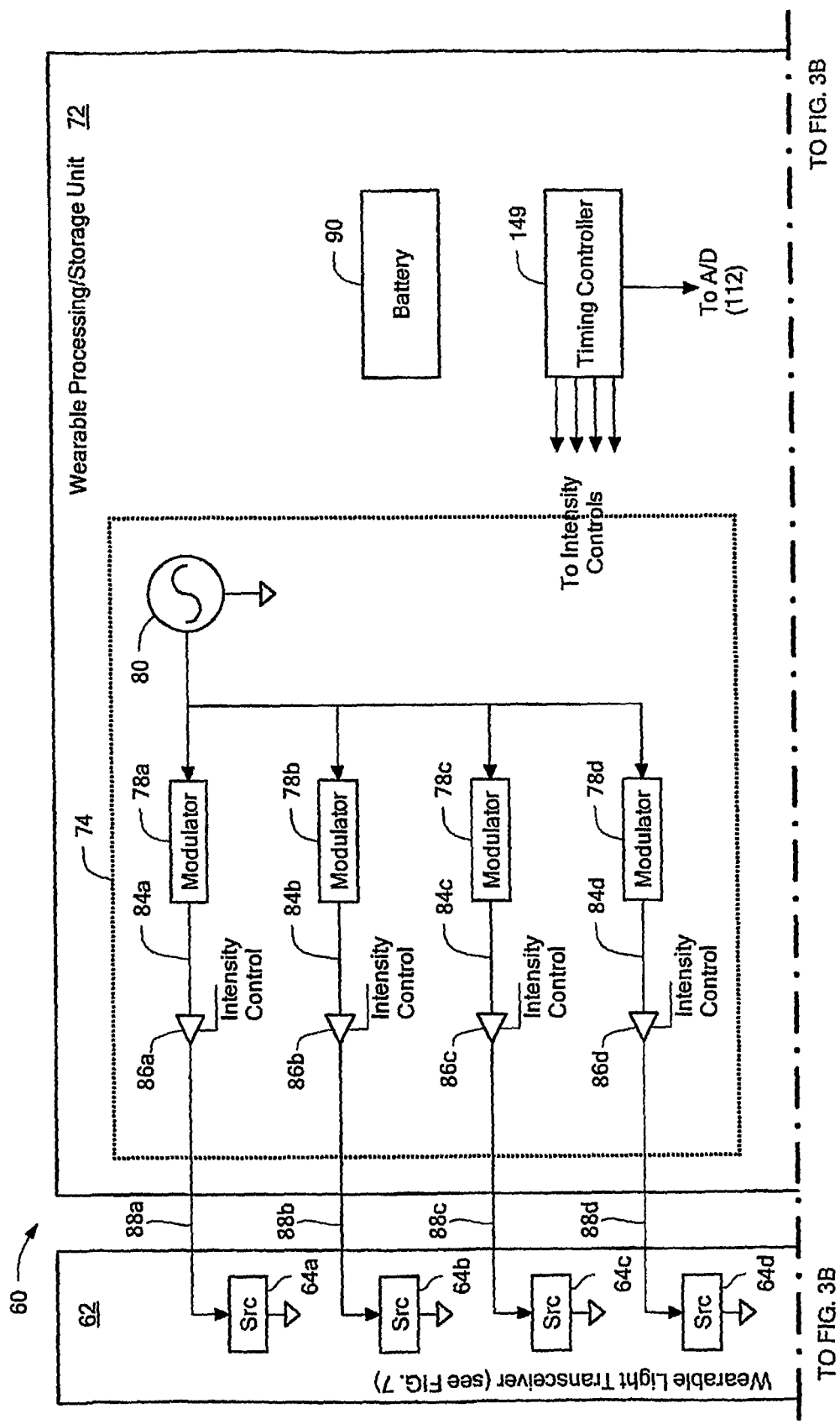
FIGS. 3A and 3B, is a block diagram showing still further details of the first portion of FIG. 1, including the light transceiver and the processing/storage unit having the signal processor and the storage device.
Figure 3B:
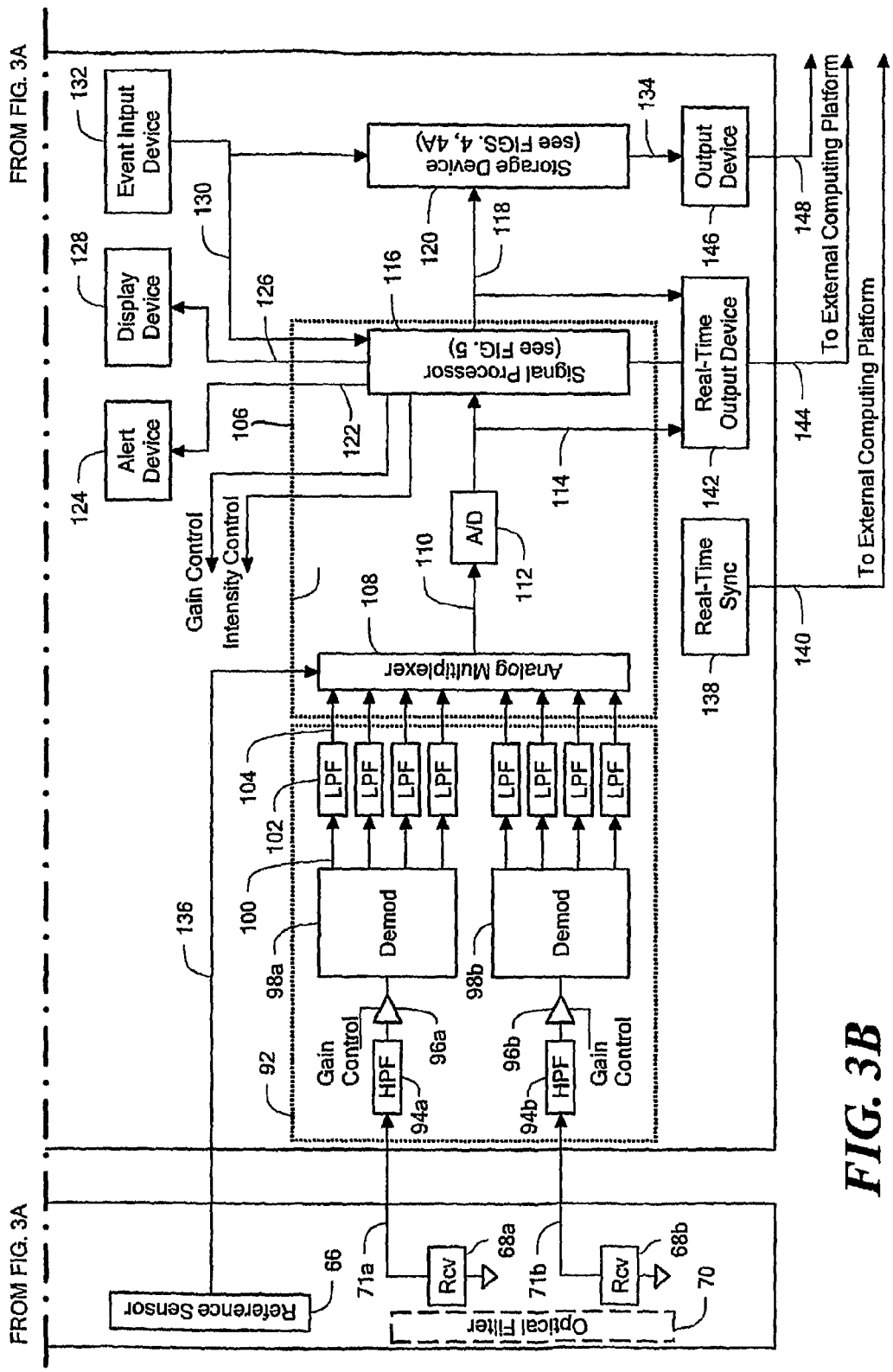

Referring now to FIG. 3, which includes FIGS. 3A and 3B, a portion of an electro-optical system 60 includes a light transceiver 62 and a processing/storage unit 72. The light transceiver 62 and the processing/storage unit 72 are provided having a size, weight, shape, and design (e.g., self-contained battery) selected such that the light transceiver 62 and the processing/storage unit 72 can be worn by a user under ambulatory conditions. The light transceiver 62 may, for example, be similar to the light transceiver 38 of FIG. 2. In the exemplary embodiment of FIG. 3, the light transceiver 62 includes four light sources 64a-64d adapted to generate transmitted light into a biological tissue of a person. The light transceiver 62 also includes two light receivers 68a, 68b adapted to receive intrinsic light exiting the biological tissue and adapted to generate respective transceiver output signals 71a, 71b in response to the received light.

In one particular embodiment, two of the light transmitters 64a-64d transmit light having a first wavelength of approximately 690 nanometers and two of the light transmitters transmit light having a second wavelength of approximately 830 nanometers, i.e., different colors. These wavelengths are in the red or near-infrared region, which is known to propagate well in biological tissue. At a particular time, a first measurement can be made, wherein one of the light transmitters (e.g., 64a) transmits light having the first wavelength into tissue near one of the two light detectors (e.g., 68a). At the same time, another one of the other light transmitters (e.g., 64b) transmits light having the second wavelength into tissue near the same one of the two light detectors (e.g., 68a). As a result, light received by the light detector (e.g., 68a) provides a single-point, two-color measurement. At the same or another particular time, a second measurement can be made, wherein another one of the light transmitters (e.g., 64c) transmits light having the first wavelength into the tissue near another one of the two light detectors (e.g., 68b). At the same time, another one of the light transmitters (e.g., 64d) transmits light having the second wavelength into the tissue near the same another one of the two light detectors (e.g., 68b). As a result, light received by the light detector 68b provides another single-point, two-color measurement.

It should be recognized that the light transmitters (e.g., 64a, 64b) and the light receiver (e.g., 68a) can be placed an arbitrary distance from the light transmitters (e.g., 64c, 64d) and the light receiver (e.g., 68b). Therefore, the two single-point, two-color measurements described above can be at arbitrary separations on the tissue.

The different colors can allow, for example, a separate determination of the concentration of oxyhemoglobin and deoxyhemoglobin. This can be achieved by measurement of tissue absorption at each wavelength and, using diffusion theory, converting these measurements to concentrations using a form of the known Beer-Lambert law.

In another embodiment, the four light transmitters 64a-64c transmit light having four different wavelengths (e.g., 690 nm, 750 nm, 830 nm, 915 nm), also in the red or near-infrared region. In one particular embodiment, the four light transmitters 64a-64d transmit at the same time, resulting in four wavelengths of light received at the two light receivers 68a, 68b at the same time. With four colors, using the Beer-Lambert approach, one can separately determine the concentrations four tissue components, for example, oxyhemoglobin, deoxyhemoglobin, water, and lipid.

In some embodiments, the light sources 64a-64d are light emitting diodes. However, in other embodiments, the light sources 64a-64d can be another type of light sources, for example, laser diodes, incandescence, halogen, tungsten lamps.

In some embodiments, the light receivers 68a, 68b are semiconductor photodetectors (e.g., photo diodes or phototransistors). However, in other embodiments, the light receivers 68a, 68b can be another type of light receiver, for example, photoresistors, photo multiplier tubes, or charge coupled devices.

The light transceiver 62 can also include a reference sensor 66. The reference sensor 66 can include one or more of sensors selected form a group including, but not limited to, a motion sensor, a strain gauge, a temperature sensor, and an accelerometer, piezoelectric sensor, impedance sensor, and an induction sensor.

The light transceiver 62 can also include an optional optical filter 70, to limit the spectral characteristics of light incident on the light receivers 68a and 68b. In one embodiment, the optical filter 70 can filter out (exclude) colors associated with light sources 64a-64d to enable measurement of a fluorescent marker.

The processing/storage unit 72 may, for example, be similar to the processing/storage unit 44 described above in conjunction with FIG. 2. The processing/storage unit 72 includes a power source (e.g., battery) 90 adapted to power the first portion 60 for a substantial period of time, for example, twenty-four hours or forty-eight hours. In some embodiments, portions of the light transceiver 62 and/or the processing/storage unit 72 are powered on only from time to time, for example, for ten seconds each minute, or for a short period following a manual indication upon an event input device 132 (described more fully below), in order to extend the amount of time for which the power source 90 can power the unit.

The processing/storage unit 72 further includes a modulator portion 74, which can have a signal source 80 (e.g. an oscillator), four modulators 78a-78d and four intensity controlled amplifiers 86a-86d, adapted to generate four frequency signals 88a-88d coupled to the light sources 64a-64d. The modulator portion 74 can correspond, for example, to the modulator portion 46 of FIG. 2.

In one particular embodiment, the modulators 78a-78d are frequency sources each operating at a different frequency, which generate the frequency signals 88a-88d at different frequencies. Therefore, in one particular embodiment, in response to the frequency signals 88a-88d, the light sources 64a-64d can transmit amplitude modulated transmitted light, each at a different modulation frequency.

The processing/storage unit 72 further includes a demodulator portion 92, which can have two high pass filters (HPFs) 94a, 94b, two gain controlled amplifiers 96a, 96b and two demodulators 98a, 98b. Each of the demodulators 98a, 98b can provide at least four output signals (e.g., output signal 100) in accordance with the four light transmitters 64a-64d to four respective low pass filters (LPFs) (e.g., low pass filter 102). Each low pass filter provides a demodulated signal (e.g., demodulated signal 104). The demodulator portion 92 can correspond, for example, to the demodulator 48 of FIG. 2.

In one particular embodiment, each of the demodulators 98a, 98b are amplitude demodulators, each of which can demodulate a received signal received by a respective light receiver 68a, 68b, into four demodulated signal (e.g., demodulated signal 104), each one of which is associated with a respective one of the light sources 64a-64d and a respective one of the associated amplitude modulated transmitted light signals described above. Therefore, each one of the demodulator outputs is representative of light received resulting from transmitted light from one of the light sources 64a-64d. With this arrangement, it should be recognized that each one of the demodulators 98a, 98b, for example, the demodulator 98a, can provide four demodulated output signals.

It will, however, be understood that the demodulators 98a, 98b can each generate eight output signals rather than the four output signals shown. For example, the demodulator 98a can provide four output signals representative of amplitude and four output signals representative of phase. Application of the amplitude and phase signals is further discussed below.

The processing/storage unit 72 still further includes a processing portion 106, having an analog multiplexer 108, which provides a multiplexed signal 110. An analog to digital (A/D) converter 112 receives the multiplexed signal 110 and generates a converted signal 114. A timing controller 149 can control the A/D converter 112 and the light sources 64a-64d, for example, by way of the intensity controlled amplifiers 86a-86d, providing transmission of light by the light sources 64a-64d at a predetermined light transmission rate and with a predetermined light transmission on/off duty cycle (i.e., a predetermined "on" time) and also providing an associated sampling by the A/D converter 112 at a predetermined sampling rate. The timing controller 149 can control the light sources 64a together so that the light sources 64a-64d have the same light transmission rate and duty cycle, or separately, so that at least some of the light sources 64a-64d have different light transmission rates and/or duty cycles.

In some embodiments the converted signal 114 includes signal samples having a sample rate of at least 0.1 samples per second and the light transmission rate is the same rate. In other embodiments, the sample rate of the converted signal 114 is higher, for example, at least two times a heartbeat rate of a person to whom the wearable light transceiver 62 is coupled, and the light transmission rate is the same rate. In still other embodiments, the sample rate of the converted signal 114 is still higher, for example, at least ten samples per second, and the light transmission rate is the same rate. However, in still other embodiments, the sample rate of the converted signal 114 can be higher or lower than the light transmission rate. The light transmission duty cycle of the light sources 64a-64d can be selected based upon a variety of factors, including but not limited to, a sensitivity of the light receivers 71a, 71b, an intensity of the light sources 64a-64d, and a depth being probed into the tissue. In some embodiments, the light transmission duty cycle is approximately fifty percent. However, in other embodiments, the light transmission duty cycle can be less than fifty percent or greater than fifty percent, for example, twenty-five percent or seventy-five percent. In some embodiments, the light transmission duty cycle is adaptive, wherein a magnitude of the received signal 71a and/or 71b (or converted signal 114) can be used to increase or decrease the light transmission duty cycle according to the magnitude. For example, a low magnitude can result in a higher light transmission duty cycle.

A signal processor 116 receives the converted signal 114 and generates a processed signal 118. The signal processor 116 can correspond, for example, to the signal processor 50 of FIG. 2. It will be understood that the converted signal 114 is a time-sampled, combined, digitized version of the transceiver output signals 71a, 71b, once demodulated, containing a sequence of time samples from each of the demodulator outputs. The processed signal 118 is received by a storage device 120 and stored as a stored-processed signal. The storage device 120 can correspond, for example, to the storage device 52 of FIG. 2.

Like the converted signal 114, in some embodiments the processed signal 118, which is stored in the storage device 120, includes signal samples having a sample rate of at least 0.1 samples per second. In other embodiments, the sample rate is higher, for example, at least two times a heartbeat rate of a person to whom the wearable light transceiver 62 (FIG. 2) is coupled. In still other embodiments, the sample rate is still higher, for example, at least ten samples per second.

In some embodiments, the storage device 120 comprises a solid-state memory. In other embodiments, the storage device comprises a data storage device, for example, an MP3 recorder. However, a variety of different storage devices can be used.

The signal processor 116 can generate an alert signal 122, which can be communicated to an alert device 124. The alert device 124, can be, for example, a light, a bell, a buzzer, or the like. The signal processor 116 can also generate a display signal 126, which can be communicated to a display device 128. The display device 128 can be, for example, a liquid crystal display (LCD), a light emitting diode (LED) display, or the like. The signal processor 116 can also receive an event signal 130 from an event input device 132. The event input device 132 can be, for example, a push button, switch or the like. The event signal 130 can also be provided to the storage device 120 for reasons described more fully in conjunction with FIGS. 4 and 4A below.

The processing/storage unit 72 yet further includes one or more of a real-time output device 142, an output device 146, and a real-time sync module 138. Operation of these devices is described below.

In operation, the modulator portion 74 generates the four frequency signals 88a-88d, each at a different frequency, in response to which the light sources 64a-64d generate four amplitude modulated transmitted light signals. As described above, the light sources can generate light at the same time or at different times. The transmitted light propagates as intrinsic light within the person and exits the person as received light, which is received by the light receivers 68a, 68b. In some embodiments, the received light can pass first through the optical filter 70. In response to the received light, the light receivers generate transceiver output signals 71a, 71b. The demodulator portion 92 provides at least four demodulated signals (e.g., 102, 104) from each of two demodulators 98a, 98b in response to the transceiver output signals 71a, 71b. Each demodulated signal is representative of an amplitude of received light at one of the light receivers 68a, 68b, which is associated with a respective one of the light sources 64a-64d. Therefore, the demodulators 98a, 98b act to separate information associated with the four light sources 64a-64d.

As described above, in another embodiment, the demodulator portion 92 provides eight demodulated signals from each of two demodulators 98a, 98b rather than four, wherein four of the demodulated signals are representative of an amplitude of received light at one of the light receivers 68a, 68b and another four of the demodulated signals are representative of a phase of received light at one of the light receivers 68a, 68b.

The analog multiplexer 108 in combination with the A/D converter 112 provide converted signal 114 to the signal processor 116, which processes the converted signal. As described more fully below in conjunction with FIG. 5, the signal processor 116 can perform a variety of processing, including, but not limited to, sorting the sequence of time samples within the converted signal 114, automatically measuring physiological parameters and automatically detecting physiological events in response to the transceiver output signals 71a, 71b.

The signal processor 116 can generate the processed signal 118, which is stored as the stored-processed signal in the storage device 120. The stored-processed signal can have a variety of forms, including, but not limited to, a sorted or unsorted version of the converted signal 114, a version of the converted signal 114 which is simply processed to remove signal artifacts (more fully described below), a measurement signal representative of a measurement made by the signal processor 116 in response to the transceiver output signals 71a, 71b, and a detection signal representative of a detection of a physiological event made by the signal processor 116 in response to the transceiver output signals 71a, 71b. The measurement signal and the detection signal generated by the signal processor 116 are discussed in greater detail below in conjunction with FIG. 5.

The real-time output device 142 can provide one or both of the converted signal 114 and the processed signal 118 as a real-time signal 144 to the external computing platform 56 (FIG. 2). The output device 146 can provide the stored-processed signal 134 as a stored-processed signal 148 to the external computing platform 56 (FIG. 2). In one particular embodiment, the stored-processed signal 146 is provided to the external computing platform 56 as a download of the stored-processed signal 134 from time to time or upon command.

The real-time sync module 138 can provide a real-time sync signal 140 to the external computing platform, allowing synchronization with other instruments, for example, an electrocardiogram (EKG) instrument and/or and electroencephalogram (EEG) instrument. Synchronization allows for physiological events detected and/or measured by a variety of instruments to be more easily compared.

In some embodiments, the signals 140, 144, 148 are provided as wireless signals to the external computing platform 56. In other embodiments, the signals 140, 144, 148 are provided as directly wired signals to the external computing platform 56. In still other embodiments, the signals 140, 144, 148 are provided as indirectly wired signals to the external computing platform 56, for example, as Internet protocol (IP) signals on the Internet.

The display device 128 can provide a display of the above-described measured signal generated by the signal processor 116 and/or a display of the detection signal generated by the signal processor 116. The event input device 132, for example, a push button, can be pressed by a person wearing the first portion 60, or by any other person, in order to inject a time tag into the processed signal and/or into the stored processed signal within the storage device 120. While one event input device is shown, other embodiments can have more than one event input device, wherein event signals generated by respective ones of the event input devices are indicative of different events indicated by the user, for example, a dizzy spell versus a heart arythmia.

The signal processor 116 can provide an intensity control signal to the modulator portion 74 to maintain precise amplitude control of the frequency signals 88a-88d.

The modulators 78a-78d are described above to generate frequency signals 88a-88d in order to amplitude modulate the light sources 64a-64b, each operating at a different frequency. Similarly, the demodulators 98a, 98b are described to be amplitude demodulators, each of which provide at least four output signals (e.g., output signal 100). In some embodiments, the modulators 78a-78d generate the frequency signals 88a-88d at relatively low frequencies (and preferably non-multiples of one another and non-multiples of 50 Hz or 60 Hz), for example, 205 Hz, 374 Hz, 543 Hz, and 712 Hz, and the demodulators 98a, 98d demodulate accordingly. However, in other embodiments, the modulators 78a-78d generate the frequency signals 88a-88d at relatively high frequencies, for example, 70.0 MHz, 70.1 MHz, 70.2 MHz and 70.3 MHz, and the demodulators 98a, 98d demodulate accordingly. However, any modulation frequencies can be used.

It will be understood that, when operating with relatively high modulation frequencies, the above-described arrangement for which the demodulators 98a, 98b generate both amplitude and phase output signals (i.e., each demodulator 98a, 98b generates eight output signals), the amplitude signals are representative of absorption of the intrinsic light, while the phase signals are representative of scattering of the intrinsic light. The signal processor 116 can be adapted to use both absorption and scattering information as is further discussed below in conjunction with FIG. 5.

A description of generation of absorption and scattering from measured amplitude and phase is described, for example in Arridge, S R (1999) Optical Tomography in Medical, Imaging Inverse Problems 15: R41-R93.

It will be understood that signal amplitude attenuation is generally representative of total absorption of photons along their full propagation path length in a medium, and phase signals are generally representative of an average path length when photons propagate through a highly scattering medium. Tissue optical absorption and scattering properties can be derived from the above-described amplitude signal and phase signal using transport or diffusion theory.

It will be further understood that the tissue absorption properties are generally representative of a concentration of a compound within the biological tissue. More specifically, the compound can include, but is not limited to, oxyhemoglobin, deoxyhemoglobin, water, lipid, cytochrome oxidase, and fluorescently molecules or other introduced molecules, which absorb in the near-infrared.

It will also be understood that the tissue scattering properties can be used to reveal other sorts of tissue information such as bone density and fat content.

While four light sources 64a-64d and associated elements of the modulator portion 74 are shown, in other embodiments, there can be more than four or fewer than four light sources and associated elements. For embodiments, where there are more than four or fewer than four light sources, each one of the demodulators 98a, 98b can generate a corresponding more than four or fewer than four output signals (or double this number if both amplitude and phase signals are generated).

While two light receivers 68a, 68b and associated elements of the demodulator portion 92 are shown, in other embodiments, there can be more than two or fewer than two light receivers and associated demodulator elements.

While each one of the demodulators 98a, 98b is shown to have four output signals, in other embodiments, each one of the demodulators 98a, 98b can generate more than four or fewer than four output signals, for example, four amplitude signals and four phase signals as described above.

In some embodiments, the light sources 64a-64d transmit light having a light power in the range of two to twenty milliwatts with a modulation amplitude in the range of ten to one hundred 100 percent.

In some embodiments, the light sources 64a-64d can act as stimuli to fluorescent light generated in the biological tissue. As described above, the fluorescent light is generated in response to intrinsic light associated with transmitted light generated by the light sources 64a-64d. To this end, the optical filter 70 is of particular value, allowing the fluorescent light exiting the biological tissue to be received by the light receivers 68a, 68b, while blocking the intrinsic light, which also exits the biological tissue.

While the above modulator and demodulator portions 74, 92, respectively, are described in one form, it will be understood that, when the light sources 64a-64d are amplitude modulated at very high frequencies, the demodulator portion 92 can employ homodyne or heterodyne techniques, familiar to one of ordinary skill in the art.

While particular arrangements are described above in which, at a particular time, two light sources transmit light having two respective wavelengths and four light sources transmit light having four respective wavelengths, in other embodiments having different numbers of light transmitters and light receivers, at a particular time, more than four or fewer than four wavelengths can be transmitted. Furthermore, transmitted light can have other wavelengths generally in the 500 nanometer to 1000 nanometer range.

While the modulator portion 74 is described to provide amplitude modulated transmitted light, in another embodiment, the modulator portion 74 can provide time division multiplexed (TDM) transmitted light. In these embodiments, the demodulator portion 92 is a TDM demodulator. For this arrangement, the above-described phase information can be derived from time-delays.

Gain control can be provided at amplifiers 96a, 96b to ensure a good signal-to-noise ration (SNR) for different subjects under test.

Figure 4:
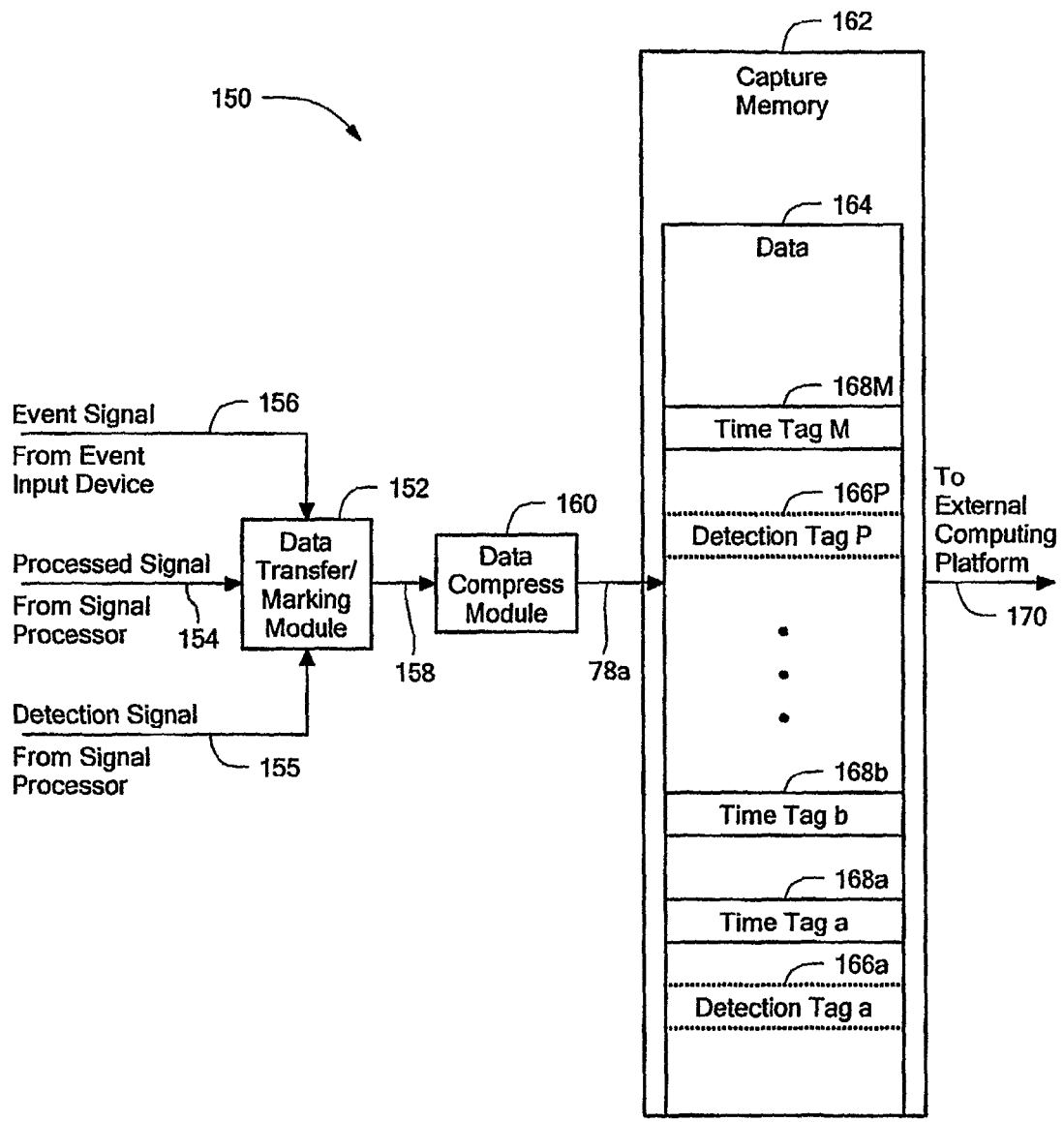
FIG. 4 is a block diagram showing further details of the storage device of FIGS. 2 and 3.

Referring now to FIG. 4, a storage device 150, which may, for example, be the same as or similar to the storage devices 52, 120 described above in conjunction with FIGS. 2 and 3, respectively. The storage device 150 can include a data transfer/marking module 152, a data compression module 160 and a capture memory 162. The capture memory 162 can store the above-described stored-processed signal as stored-processed data 164. The stored-processed data 164 can include one or more detection tags, 166a-166P and one or more time tags 168a-168M.

In operation, processed data, for example the processed signal 118 of FIG. 3 generated by the signal processor 116 of FIG. 3, is received by the data transfer/marking module 152. As described above, the processed signal 154 (118, FIG. 3) can be in one or more of a variety of forms, including, but not limited to, a sorted or unsorted version of the converted signal 114 (FIG. 3), a version of the converted signal 114 which is simply processed to remove signal artifacts (described below), a measurement signal representative of a measurement made by the signal processor 116 (FIG. 3) in response to the transceiver output signals 71a, 71b (FIG. 3), and a detection signal 155 representative of a detection of physiological event made by the signal processor 116 in response to the transceiver output signals 71a, 71b. When the detection signal 155 indicates a detection of a physiological event by the signal processor 116 (FIG. 3), an associated detection tag (e.g., detection tag 166a) can be inserted into the stored-processed data 164.

At least one event signal 156 can also be received by the data transfer/marking module 152 from a respective at least one event input device, for example, the event input device 132 of FIG. 3. The processed data 154 generally passes straight though the data transfer/marking module 152 and is stored as stored-processed data 164. However, upon any manual indication of an event upon the event input device 132 (FIG. 3), a time tag, (e.g., the time tag 168a) can be inserted into the processed data 154, and is stored along with the processed data 164. Where more than one event input device is provided, the time tag can also indicate which event input device was used to generate the time tag.

It will be recognized that either the person wearing the first portion 60 (FIG. 3) or another person can generate the event signal 156 with the event input device 132. The event signal 156 can be generated by the person in response to a physiological event of which the person is aware, for example, a dizzy spell or a hearth arrhythmia. With this arrangement, upon playback of the stored-processed data 164, regions of interest associated with the time tags 168a-168M can be identified and scrutinized by further processing as provided, for example, by the external computing platform 56 of FIG. 2.

The data compression module 160 can compress the processed data in any one of a number of data compression methods, for example, FAN, AZTEC or CORTES algorithms, or MPEG, WAV, WMA, Ogg, AAC, or AC-2 formats, which are typically associated with audio files. The resulting data compression allows a greater amount of data to be stored.

In some embodiments, the capture memory 162 is sized to be able to store at least four hours of the processed signal (either compressed or uncompressed), wherein the stored-processed signal has a stored signal duration sufficient to detect an intermittent medical condition of the person, having an occurrence period of at least four hours. In other embodiments, the capture memory 162 is sized to be able to store more than twenty-four hours of the processed signal (either compressed or uncompressed), wherein the stored-processed signal has a stored signal duration sufficient to detect an intermittent medical condition of the person, having an occurrence period of at least four hours. In still other embodiments, the capture memory 162 is sized to be able to store more than forty-eight hours of the processed signal (either compressed or uncompressed), wherein the stored-processed signal has a stored signal duration sufficient to detect an intermittent medical condition of the person, having an occurrence period of at least four hours.

As described above, in some embodiments the processed signal 154, which is stored in the storage device 150, includes signal samples having a sample rate of at least 0.1 samples per second. In other embodiments, the sample rate is higher, for example, at least two times a heartbeat rate of a person to whom the wearable light transceiver 62 (FIG. 2) is coupled. In still other embodiments, the sample rate is still higher, for example, at least ten samples per second.

While the data transfer/marking module 152 and the data compression module 160 are shown to be in a certain coupling arrangement, it will be appreciated that the data transfer/marking module 152 and the data compression module 160 can be coupled in other arrangements.

In some embodiments, the data transfer/marking module 152 and/or the data compression module 160 are not used, and therefore, the time tags and/or the detection tags are not stored.

Figure 4A:
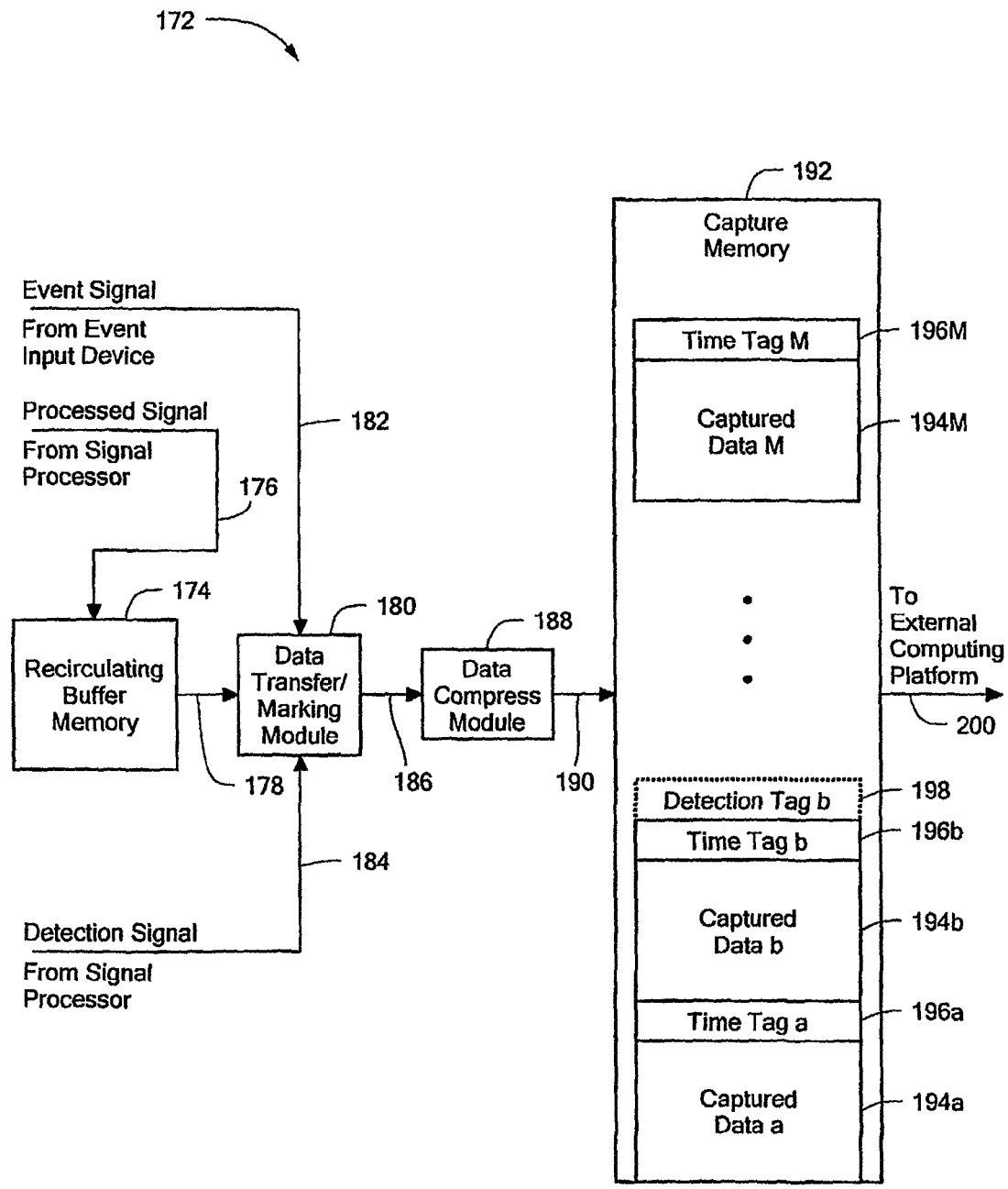
FIG. 4A is a block diagram showing details of an alternate embodiment of the storage device of FIGS. 2 and 3.

Referring now to FIG. 4A, an alternate storage device 172 can correspond, for example, to the storage devices 52, 120 of FIGS. 2 and 3, respectively. The storage device 172 can include a recirculating buffer memory 174, a data transfer/marking module 180, a data compression module 188, and a capture memory 192. The capture memory 192 can store the above-described stored-processed signal as data in the capture memory 192. The data in the capture memory can include one or more data portions 194a-194M, one or more detection tags 198, and one or more time tags 196a-196c.

In operation, processed data 176, for example, the processed signal 118 of FIG. 3, generated by the signal processor 116 of FIG. 3, is received by the recirculating buffer memory 174. The recirculating buffer memory 174 is sized to hold a fixed amount of recirculating information, for example, one hour of the processed signal 176. In response to an indication by a manual event signal 182 generated by a person upon the event input device, for example, the event input device 132 of FIG. 3, or in response to an indication by the detection signal 184 generated by the signal processor, for example, the signal processor 116 of FIG. 3, data in the recirculating buffer memory 174 is moved to the capture memory 192. The data in the recirculating buffer memory 174 passes through the data transfer/marking module 180.

As described above, the processed signal 176 (118, FIG. 3), which is stored in the recirculating buffer memory 174, can be in one or more of a variety of forms, including, but not limited to, a sorted or unsorted version of the converted signal 114 (FIG. 3), a version of the converted signal 114 which is simply processed to remove signal artifacts (described below), a measurement signal representative of a measurement made by the signal processor 116 (FIG. 3) in response to the transceiver output signals 71a, 71b (FIG. 3), and a detection signal 184 representative of a detection of physiological event made by the signal processor 116 in response to the transceiver output signals 71a, 71b. When the detection signal 184 indicates a detection of a physiological event by the signal processor 116 (FIG. 3) an associated detection tag (e.g., detection tag 198b) can also be inserted into the data stored in the capture memory 192.

At least one event signal 182 can also be received by the data transfer/marking module 180 from a respective at least one event input device, for example the event input device 132 of FIG. 3. The processed data 176 generally passes straight though the data transfer/marking module 152 and is stored as stored-processed data in the capture memory 192. However, upon any manual indication upon the event input device 132 (FIG. 3) of an event, a time tag, (e.g., the time tag 196a) is inserted into the processed data 176, and is stored along with the processed in the capture memory 192. Where more than one event input device is provided, the time tag can also indicate which event input device was used to generate the time tag.

It will be recognized that either the person wearing the first portion 60 (FIG. 3) or another person can generate the event signal 182 with the event input device 132. The manual indication can be generated by the person in response to a physiological event of which the person is aware, for example, a dizzy spell or a hearth arrhythmia. With this arrangement, upon playback of the stored-processed data in the capture memory 192, regions of interest associated with the time tags 196a-196M can be identified and scrutinized by further processing as provided, for example, by the external computing platform 56 of FIG. 2.

The data compression module 188 can compress the processed data in any one of a number of data compression methods, for example, FAN, AZTEC and CORTES algorithms, or MPEG, WAV, WMA, Ogg, AAC, and AC-2 format, which are typically associated with audio files. The resulting data compression allows a greater amount of data to be stored.

In some embodiments, the capture memory 192 is sized to be able to store at least four hours of the processed signal (either compressed or uncompressed), wherein the stored-processed signal has a stored signal duration sufficient to detect an intermittent medical condition of the person, having an occurrence period of at least four hours. In other embodiments, the capture memory 192 is sized to be able to store more than twenty-four hours of the processed signal (either compressed or uncompressed), wherein the stored-processed signal has a stored signal duration sufficient to detect an intermittent medical condition of the person, having an occurrence period of at least four hours. In still other embodiments, the capture memory 192 is sized to be able to store more than fort-eight hours of the processed signal (either compressed or uncompressed), wherein the stored-processed signal has a stored signal duration sufficient to detect an intermittent medical condition of the person, having an occurrence period of at least four hours.

As described above, in some embodiments the processed signal 176, which is stored in the storage device 172, includes signal samples having a sample rate of at least 0.1 samples per second. In other embodiments, the sample rate is higher, for example, at least two times a heartbeat rate of a person to whom the wearable light transceiver 62 (FIG. 2) is coupled. In still other embodiments, the sample rate is still higher, for example, at least ten samples per second.

The recirculating buffer memory can be used in a variety of ways. For example, when the event signal 182 has a manual indication of a physiological event, and/or the detection signal 184 indicates detection of a physiological event, the contents of the recirculating buffer memory 174 can immediately begin transfer to the capture memory. However, in other embodiments, the recirculating buffer memory 176 can continue to recirculate for a period of time before beginning transfer to the capture memory rather than beginning immediate transfer. With these arrangements, as a result, data segments, for example, data segment 194a stored in the capture memory 192 can include data both before and after the occurrence of the event or detection.

While the recirculating buffer memory 174, the data transfer/marking module 180, and the data compression module 188 are shown to be in a certain coupling, it will be appreciated that the recirculating buffer memory 174, the data transfer/marking module 180, and the data compression module 188 can be coupled in other arrangements.

In some embodiments, the data transfer/marking module 180 and/or the data compression module 188 are not used, and therefore, the time tags and/or the detection tags are not stored.

Figure 5:
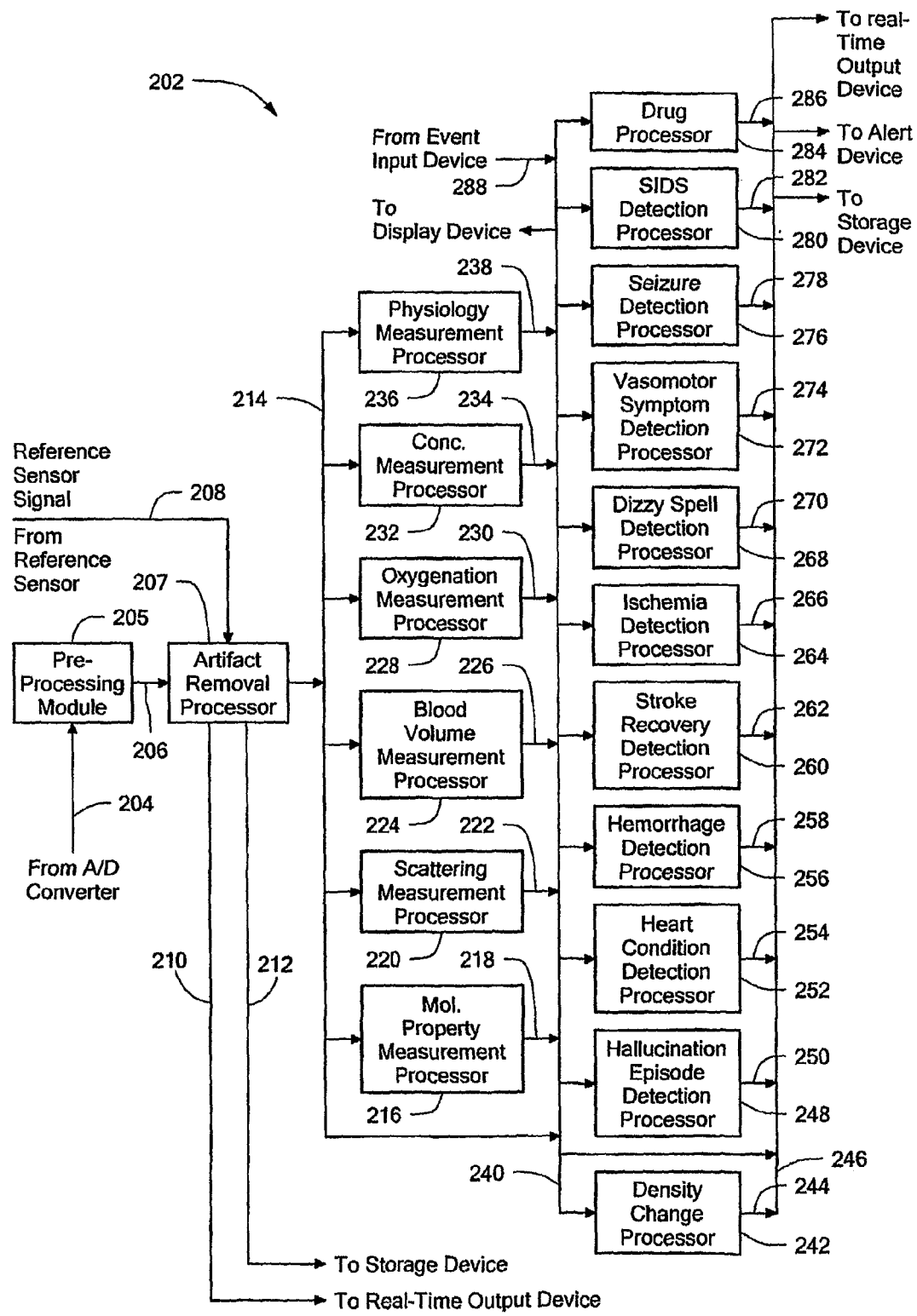
FIG. 5 is a block diagram showing further details of the signal processor of FIGS. 2 and 3.

Referring now to FIG. 5, a signal processor 202 can be the same as or similar to the signal processor 116 of FIG. 3. The signal processor 202 can include a variety of processing functions, including, but not limited to, one or more of a pre-processing module 205, an artifact removal processor 207, a molecule property measurement processor 216, a scattering measurement processor 220, a blood volume measurement processor 224, an oxygenation measurement processor 228, a concentration measurement processor 234, a physiology measurement processor 236, a drug pharmacodynamics (PD) and pharmacokinetics (PK) processor 284, or more simply, drug processor 284, a sudden infant death syndrome (SIDS) detection processor 280, a seizure detection processor 276, a vasomotor (hot flash) detection processor 272, a dizzy spell detection processor 268, an ischemia (e.g., stroke) detection processor 264, a stroke recovery detection processor 260, a hemorrhage detection processor 256, a heart condition detection processor 252, a hallucination episode detection processor 248, and a density change processor 242.

The pre-processing module 205 is adapted to perform a variety of functions, for example sorting and/or filtering of the converted signal 114 of FIG. 3. The artifact removal processor 207 is adapted to remove an artifact from the transceiver output signal (e.g., 71a, FIG. 3), or more particularly, from the converted signal 114, and to provide a clean signal 214 having reduced artifacts. The physiology measurement processor 223 is adapted to measure at least one of a heart rate, a respiration rate, a Mayer wave, a heart beat interval, a respiration interval, or a Mayer wave period of the person in response to the transceiver output signal and to generate a corresponding output signal 238. The concentration measurement processor 232 is adapted to measure a concentration of at least one of oxyhemoglobin, deoxyhemoglobin, water, cytochrome, lipid, or a fluorescent molecule in the body in response to the transceiver output signal and to generate a corresponding output signal 234. The oxygenation measurement processor 228 is adapted to measure a tissue oxygenation of the person in response to the transceiver output signal and to generate a corresponding output signal 230. The blood volume measurement processor 224 is adapted to measure a blood volume of the person in response to the transceiver output signal and to generate a corresponding output signal 226. The scattering measurement processor 220 is adapted to measure a scattering characteristic of the person in response to the transceiver output signal and to generate a corresponding output signal 222. The molecule property measurement processor 216 adapted to measure the change in at least one of a concentration, a lifetime, or a quantum yield of a fluorochrome molecule in the body of the person in response to the transceiver output signal and to generate a corresponding output signal 218.

The drug processor 284 is adapted to measure at least one of a pharmacodynamic characteristic or a pharmacokinetic characteristic of a drug in response to the transceiver output signal and to generate an output signal 286 indicative of the measurement. The sudden infant death syndrome (SIDS) detection processor 280 is adapted to detect and quantify a drop in oxygenation level of the person (infant) in response to the transceiver output signal and to generate an output signal 282 indicative of the event. The vasomotor symptom detection processor 272 is adapted to detect and quantify a vasomotor symptom of the person in response to the transceiver output signal and to generate an output signal 274 indicative of the vasomotor symptom. The dizzy spell detection processor 268 is adapted to detect and quantify a dizzy spell of the person in response to the transceiver output signal and to generate an output signal 270 indicative of the dizzy spell. The ischemia detection processor 264 is adapted to detect and quantify ischemia (e.g., stroke) of the person in response to the transceiver output signal and to generate an output signal 266 indicative of the ischemia. The stroke recovery detection processor 260 is adapted to characterize and quantify a recovery from stroke of the person in response to the transceiver output signal and to generate an output signal 262 indicative of the stroke recovery. The hemorrhage detection processor 256 is adapted to detect and quantify a hemorrhage of the person in response to the transceiver output signal and to generate an output signal 258 indicative of the hemorrhage. The heart condition detection processor 252 is adapted to detect and quantify a heart condition of the person in response to the transceiver output signal and to generate an output signal 254 indicative of the heart condition. The hallucination episode detection processor 248 is adapted to detect and quantify characteristic brain activity associated with a hallucination of the person in response to the transceiver output signal and to generate an output signal 250 indicative of the episode. The density change processor 244 is adapted to detect and quantify a density change in the biological tissue in response to the transceiver output signal and to generate an output signal 244 indicative of the density change.

More particularly, the artifact removal processor can remove unwanted characteristics (artifacts) of the converted signal 204 (114, FIG. 3). It should be recognized that the transceiver output signals (e.g., 71$a$, 71$b$ of FIG. 34) are greatly influenced by a variety of factors generally related to movement of the light transmitters 64$a$-64$d$ (FIG. 3) or light receivers 68$a$, 68$b$ (FIG. 3) relative to the person to which they are coupled. The variety of factors can include, but are not limited to, physical movement of the light transmitters 64$a$-64$d$ or light receivers 68$a$, 68$b$, movements of the person, swallowing by the person, a valsalva maneuver by the person, coughing by the person, sneezing by the person, changing facial expression by the person, changing position by the person in a way that would affect blood pressure, and breathing by the person. The above variety of factors tends to generate physiological variations in the person, which generate unwanted variation in the transceiver output signals 71$a$, 71$b$, described more fully below. The variety of factors can also be related to environmental effects, for example, temperature and humidity. Artifacts are described in greater detail below in conjunction with FIGS. 6-6C.

It will become apparent in the discussion below in conjunction with FIGS. 6-6C that some of above-identified factors tend to result in artifacts in the signal 204 that have identifiable time-domain and/or frequency-domain characteristics. Therefore, those artifacts can be identified and removed by the artifact removal processor 207 without further inputs. However, some of the above-identified variety of factors (e.g., motion) tend to result in artifacts in the signal 204 that have time-domain and/or frequency-domain characteristics that are not repeatable, or are otherwise difficult to identify or quantify. To this end, a reference sensor signal 208 from the reference sensor 66 (FIG. 3) can be used to further identify those artifacts. For example, as described above, in one particular arrangement, the reference sensor 66 is a strain gauge, and therefore, the reference sensor signal 208 is indicative of facial expressions of the person. Therefore, when a facial expression, for example, an eyebrow lifting, is detected, the artifact removal processor 207 can remove artifacts from the signal 204 (or 206), which result from the facial expression. Similarly, as described above, the reference sensor 66 can be a motion sensor, for example, a low frequency accelerometer, and the reference sensor signal 206 can be indicative of a motion of the person. Therefore, when a motion is detected, the artifact removal processor 207 can remove artifacts from the signal 204 (or 206), which result from the motion. Other types of reference sensors are described above in conjunction with FIG. 3 and their application should be readily apparent from the discussion above.

It will be apparent from discussion below in conjunction with FIG. 7, that the design of the light transceiver 14 (FIG. 1) can influence the signal artifacts. As described below, in some embodiments, the light transceiver 14 has an adhesive surface, with which it can be adhesively coupled directly to the skin of the person, reducing motion of the light transceiver 14 relative to the person and reducing the effect of facial expressions. Furthermore, the coupling 17 (FIG. 1) to the light transceiver 14, as described above, can be lightweight cable, also reducing motion of the light transceiver 14 relative to the person.

The clean signal 214 is provided by the artifact removal processor 207 to the remaining processors. The artifact removal can be achieved by adaptive filtering using the reference sensor signals, or by general signal conditioning.

The molecule property measurement processor 216 can measure at least one of a concentration, a lifetime, or a quantum yield of a fluorochrome molecule in the body. As described above, in some arrangements, light transmitted by the light sources, for example, the light sources 64$a$-64$d$, is at one or more wavelengths, the light at the one or more wavelengths excites fluorescent light from the fluorochrome at another wavelengths, and light received by the light receivers 68$a$, 68$b$ is received at the fluorescent light wavelength of the fluorochrome. To this end, the optional optical filter 70 (FIG. 3) can be selected to pass only the light at the fluorescent light wavelengths. Concentration, lifetime and quantum yield parameters of the fluorochrome can be calculated from the amplitude and phase information using photon transport theory (see e.g., Alexander D. Klose, Vasilis Ntziachristos, Andreas H. Hielscher (2005); The Inverse Source Problem Based on the Radiative Transfer Equation in Optical Molecular Imaging; Journal of Computational Physics; 202; 323-345).

In some arrangements, the fluorescent light signal is associated with a fluorochrome resulting from an injection of the fluorochrome into the person. Some types of fluorochromes, when injected into a person, tend to concentrate in particular tissues, organs, or within tumors, or attach to particular molecules. By measuring changes in the magnitude and phase of fluorescent light emanating from the tissue, the concentration, life time, or quantum yield of the fluorochromes can be determined, and associated changes in the tissue, organ, tumor, or molecule can be identified.

The molecule property measurement processor 216 can provide a measurement of a fluorescent or non-fluorescent light signal from tissue of the person for the purpose of pharmacokinetic and pharmacodynamic evaluation, as further described below.

The scattering measurement processor 220 can use phase signals, which are described more fully above in conjunction with FIG. 3, in order to measure scattering characteristics associated with the biological tissue. The scattering characteristics can be associated with a variety of physiological changes. As one example, a decrease in bone density would reduce the scattering coefficient of the bone tissue in relation to the density loss. As another example, a reduction in clear-fluid swelling (e.g. dissipation of edema) would result in an increasing scattering coefficient underlying the optical probe that exhibited a time-course of increase related to the time course of edema reduction.

The blood volume measurement processor 224 can provide a signal proportional to blood volume. This processor first calculates the concentrations of HHb and $O_2$Hb as per the oxygenation measurement processor 228 described below. The blood volume measurement processor 224 then adds these two quantities to calculate total hemoglobin (tHb), which is generally proportional to blood volume. Such measurements can be used to detect blood pooling (e.g., hemorrhage), or to quantify tissue perfusion.

The physiology measurement processor 236 can measure a variety of physiological parameters, for example, a heart rate, a heart output amplitude, a respiration rate, a Mayer wave, a heartbeat internal, a respiration interval, and a Mayer wave period. Geometry of blood vessels and average tissue blood volume changes with the heart beat cycle, which in turn results in light attenuation changes. As a result, the magnitude of received light and resulting transceiver output signal (71*a*, 71*b*, FIG. 3) will vary according to heart rate. Respiration can be measured similarly, for example, by measurement of frequency and amplitude of the changes of the magnitude of the received light (typically having a variable frequency component of 0.2-0.3 Hz, which is approximately 30% of the rate of the change of the magnitude of the received light due to cardiac oscillation). This will be more evident in the description below in conjunction with FIG. 6B.

The concentration measurement processor 232 can measure a concentration of one or more of oxyhemoglobin, deoxyhemoglobin, water, cytrochrome, lipid, and fluorescent molecules. As described above, the use of at least two different colors among the light sources (e.g., 64*a*-64*d*, FIG. 3) can allow, for example, a separate determination of concentrations of oxyhemoglobin, deoxyhemoglobin, and total hemoglobin. With data from at least three wavelengths of light, and using a similar Beer-Lambert approach, water concentrations can be computed, as water is the third most absorbing molecule in tissue in the near-infrared range (behind oxyhemoglobin and deoxyhemoglobin). Cytochrome oxidase concentrations can also be computed, to provide a measure of tissue metabolism. This will also be typically achieved with a Beer-Lambert approach and data from four or more wavelengths. Similarly, lipid and fluorescent molecule concentrations can be computed using wavelengths differentially sensitive to the absorption spectra of the species of interest. The measured concentrations can be used as independent concentration data, or by subsequent processors.

The best wavelengths (i.e., colors) to use depends on the absorption spectra of the molecular species being measured. Non-invasive measurements in deep tissues (greater than roughly 1 cm deep) typically require the use of relatively weakly absorbed wavelengths, in the range of 650 nm to 950 nm.

The oxygenation measurement processor 228 can measure an oxygenation of a biological tissue. Oxygenation is known to be determined by a ratio of oxygenated hemoglobin to a sum of oxygenated hemoglobin plus deoxygenated hemoglobin. As described above, the use of different colors among the light sources (e.g., 64*a*-64*d*, FIG. 3) can allow, for example, a separate determination of concentrations of oxyhemoglobin, deoxyhemoglobin, and total hemoglobin. Therefore, the magnitudes of light received at the two frequencies can be used to determine the above ratio. This determination can be done by calculating the oxyhemoglobin and deoxyhemoglobin concentrations separately using a version of the Beer-Lambert law as described above, and the combining these values to compute tissue oxygenation.

One or more of the measurement processors 216, 220, 224, 228, 232, 236 can provide respective measurement signals 218, 222, 226, 230, 234, 238 to the display device (128, FIG. 3).

The drug pharmacodynamics (PD) and pharmacokinetics (PK) processor 284, or more simply, drug processor 284, can measure information related to the PD and PK of a drug. For example, the molecule property measurement processor output 218 can use the fluorescent light described above to identify pharmacokinetic and pharmacodynamic related parameters of a drug. It is known that some drugs may result in tissue hemodynamic or metabolism changes, and if not already fluorescent, a fluorochrome marker can be attached to a drug or to molecules associated with the effects of a drug. When ingested, the fluorochrome marker passes into the bloodstream. By measuring the resulting specific (fluorescent) light wavelength(s) over time, biochemical and physiologic effects of drugs, the time course of absorption, distribution, metabolism, and excretion (ADME) of the drug in the body can be established. In addition, the output of the other measurement processors (218, 222, 226, 230, 234, 238) can also be used to evaluate PD and PK effects of the drug on the person.

The SIDS detection processor 260 can use, for example, the output 230 generated by the oxygenation measurement processor 228 to identify a sudden or excessive drop in oxygenation of the blood, particularly in the brain of an infant, and can generate the output signal 282 indicative of the drop. Such oxygenation drop may be indicative of SIDS onset. As an example, a drop in tissue oxygenation below 60% represents a physiologically atypical state indicative of tissue hypoxia. If such a state were detected in an infant while sleeping, SIDS would be the most likely cause.

The seizure detection processor 276 can use, for example, the output 230 from the oxygenation measurement processor 228, and/or the output 238 (e.g., heart rate) from the physiology measurement processor 236, and/or the output 226 from the blood volume measurement processor 224. As is known, during a seizure, regional blood volume increases, oxygenation decreases, and heart rate increases. For example, in one particular embodiment, one would continuously monitor for a relatively sudden (<30 sec time course) increase in heart rate that was synchronous with a drop in oxygenation and an increase in regional blood volume localized to a region of the brain previously suspected of (or predicted to generate) seizure activity. This constellation of changes, together with appropriate thresholds for significant change, and the temporal conjunction of these changes can thus be used to detect a seizure and to generate the output signal 278 indicative of the seizure.

The vasomotor symptom (hot flash) detection processor 272 can use, for example, the output 234 (e.g., oxyhemoglobin and deoxyhemoglobin concentrations) from the concentration measurement processor 232. A sum of oxyhemoglobin and deoxyhemoglobin concentrations, or output 226 from the blood volume measurement processor, as recorded from the periphery (e.g., an upper arm). As is known, during hot flashes, the peripheral blood flow increases, but this may be a non-specific type of physiological change. Therefore, in one particular embodiment, the device could be disposed to monitor the upper arm. The blood volume output 226 could be combined with an event input signal 288 from an event input device (e.g., 132, FIG. 2) and event-triggered averaging in the vasomotor symptom detection processor 272 to characterize the time course (i.e., waveform) of a hot-flash event. This characterization time course can then be used in a template-matching arrangement, without need for further event input signals, to generate the output signal 274 indicative of the hot flash.

The dizzy spell (syncope) detection processor 268 can use, for example, the output 230 from the oxygenation measurement processor 228 and/or the output 238 (e.g., heart rate and amplitude) from the physiology measurement processor 236, and can generate the output signal 270 indicative of the dizzy spell. As is known, decrease in cerebral blood flow and regional cerebral tissue oxygenation can induce a dizzy spell. A low heart rate can also be associated with a dizzy spell. Also, a fainting event associated with a dizzy spell would generate a signal in an acceleration-based motion reference sensor signal 208. Therefore, in one particular embodiment, the output 238 from the physiology measurement processor 236 and/or the output 230 from the oxygenation measurement processor 228 can be used in conjunction with the motion reference sensor signal 208 in a event-triggered fashion to characterize the multi-sensor constellation of changes (brain oxygenation drop, heart rate drop, and/or downward motion acceleration) associated with a syncope/dizzy spell. Once so characterized and stored in memory, as with the vasomotor detection processor 272, these characterization waveforms can then be used in conjunction with pattern-recognition for early detection of syncope onset, before fainting occurs. In other embodiments, the output 238 from the physiology measurement processor 236, the output 230 from the oxygenation measurement processor 228, and the motion reference sensor signal 208 can be used individually.

The ischemia detection processor 264 can use, for example, the output 230 from the oxygenation measurement processor 228 and can generate the output signal 266 indicative of the ischemia. As is known, ischemia is identified by a low oxygenation level, which is particularly important in the brain. Therefore, in one particular embodiment, these clues can be used to identify ischemia or stroke by monitoring tissue (or brain) oxygenation levels from multiple sites and comparing the measurements. Measurement sites on the body that show an oxygenation level more than a factor, for example, a factor of two, lower than the other measurement sites likely indicate the presence of an ischemic stroke.

The stroke recovery processor 260 can also use, for example, the output 230 from the oxygenation measurement processor 228 and can generate the output signal 226 indicative of the stroke recovery. In one embodiment, a brain-based hemodynamic response (increase in oxy-Hb and associated decrease in deoxy-Hb) may appear in response to external stimuli, even in the absence of behavioral responses. This characteristic can be indicative of a return to more normal brain function. As is known, a rising oxygenation level can be associated with return to normal blood flow following a stroke. Thus, in one embodiment, during the measurement of brain oxygenation from multiple sites on the head, one may observe a normalization of oxygenation measurements across measurement sites (to within approximately 20%) in response to a return of normal blood flow to a region.

The hemorrhage detection processor 256 can use, for example, the output 226 from the blood volume measurement processor 226 and can generate the output signal 258 indicative of the hemorrhage. As is known, hemorrhage is associated with blood pooling, or significant increase in regional blood volume. Therefore, in one particular embodiment, the combined information about oxyhemoglobin and deoxyhemoglobin could be used to identify hemorrhage. In one embodiment, a decrease in total optical signals (or an increase in blood volume) at one measurement site on the head that has a reduction by greater than a 50% relative to other measurement sites on the head can be indicative of a hemorrhage.

The heart condition detection processor 252 can use, for example, the output 230 from the oxygenation measurement processor 228, and/or the output 238 from the physiology measurement processor 236 (e.g., heart rate, heart beat interval), and/or the output 226 from the blood volume measurement processor 224, and can generate the output signal 254 indicative of the heart condition. As is known, heart rate and heart rate variation are important indicators of many medical conditions such as dysrythmia. A shape of the heartbeat waveform indicates the working status of the heart. Tissue blood volume and oxygenation indicates the end consequence of circulation. Therefore, in one particular embodiment, these clues can be used to monitor cardiac and circulation conditions. For example, fast but effective cardiac pumping will have a fast heartbeat rate coupled with a blood volume increase on the order of five percent. Fast and ineffective cardiac pumping (e.g., fibrillation) would also exhibit a fast heartbeat rate but blood volume may decrease by a factor of approximately four or more.

The hallucination episode detection processor 248 can use, for example, the output 230 from the blood oxygenation processor 228 and/or the output 238 from the physiology measurement processor 236 to detect cerebral oxygenation and blood flow changes indicative of an hallucination. The detected hallucination can be an auditory hallucination or another hallucination, e.g., from a schizophrenic episode. As is known, auditory hallucination is associated with distinct increases in blood flow and oxygenation changes in the brain's superior temporal cortex. Therefore, in one particular embodiment, these clues can be used to identify an auditory hallucination by a regional change in primary auditory cortex brain activity (an increase in oxy-Hb and an associated decrease in deoxy-Hb) in the absence of external auditory stimuli. Other hallucinations can be detected in similar ways.

The density change processor 242 can use, for example, the output 222 from the scattering measurement processor 220, which measures a density of a compound as described above. The density change processor 242 can measure a rate of change of the density, and can generate the output signal 244 indicative of the density change. For example, this could be used for measurement of bone density change, tissue/cell density change, fat density change, or accumulation/binding density change of a fluorescent molecule. As is known, a decrease in bone density, such as in osteoporosis, is associated with reduced optical scattering over a relatively long period of time. A decrease in fat content (such as in the weight losing procedure) is associated with increased optical scattering. Therefore, in one particular embodiment, these clues can be used to identify tissue density changes.

While a variety of processor are shown to be included in the signal processor (e.g., 116, FIG. 3), in other embodiments, fewer processors or more processors are included in the signal processor. Also, while the processors are shown to be within the signal processor 116, some or all of the processor can be within the external computing platform (56, FIG. 2), either instead of or in addition to the processors shown in the signal processor 116.

FIGS. 6-6C show graphs, each having a respective horizontal scale in units of time in minutes and a respective vertical scale in units of output (received) light power in arbitrary units (a.u.).

Referring now to FIG. 6, a curve 290 corresponds to a continuous demodulated signal (e.g., 104, FIG. 3) representative of received light, which is received, for example, by the light transceiver 68*a* of FIG. 3. The curve 290 has a feature 292 associated with a motion of the person wearing the light transceiver 62. The feature 292 is followed in time by a region 294 having an elevated light output power.

Referring now to FIG. 6A, a curve 296 corresponds to a continuous demodulated signal (e.g., 104, FIG. 3) representative of received light, which is received, for example, by the light transceiver 62 of FIG. 3. The curve 290 has a feature 298 associated with a cough by the person wearing the light transceiver 62.

Referring now to FIG. 6B, a curve 300 corresponds to a continuous demodulated signal (e.g., 104, FIG. 3) representative of received light, which is received, for example, by the light transceiver 62 of FIG. 3. The curve 300 has features typified by the feature 302, which is typical of a heartbeat of the person wearing the light transceiver 62. The curve 300 also has a repeating characteristic 304 indicative of a Mayer wave.

Referring now to FIG. 6C, a curve 306 corresponds to a continuous demodulated signal (e.g., 104, FIG. 3) representative of received light, which is received, for example, by the light transceiver 62 of FIG. 3. The curve 306 has a repeatable feature 308 associated with a Valsalva maneuver by the person wearing the light transceiver 62.

From FIGS. 6-6C, is should be apparent that the time waveforms 290, 296, 300, 306 each have distinguishable features, which would tend to degrade measurements and detections, and which can be identified and removed by the artifact removal processor 207 (FIG. 5).

Figure 7:
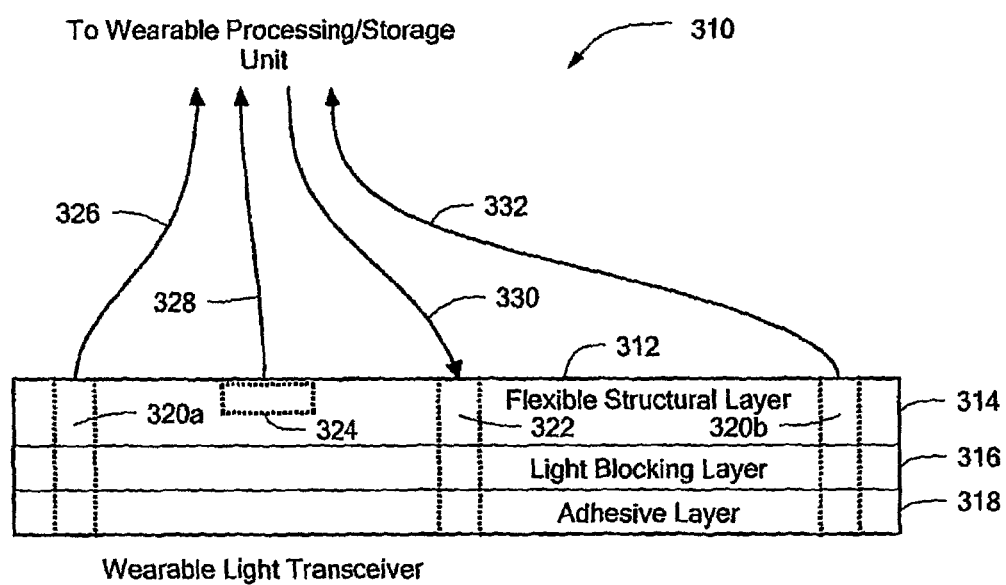
FIG. 7 is a block diagram showing further details of the light transceiver of FIGS. 1-3.

Referring now to FIG. 7, a light transceiver 312 can be the same as or similar to the light transceivers 14, 38, 62 of FIGS. 1-3, respectively. The light transceiver 312 includes a flexible structural layer 314, a light-blocking layer 316, and an adhesive layer 318. The light transceiver 312 includes light sources 320a, 320b, which can be the same as or similar to the light sources 64a-64d of FIG. 3, and a light receiver 322, which can be the same as or similar to the light receivers 68a, 68b of FIG. 3. The light transceiver 312 also includes a reference sensor, which can be the same as or similar to the light reference sensor 66 of FIG. 3. Wires 326-332, which can form a cable, couple the light transceiver 312 to the processing/storage unit (e.g., 16, FIG. 1).

As described above, the adhesive layer 318 can be used to adhesively couple the light transceiver to a person, for example, the skin of a person. The adhesive coupling results in reduced signal artifacts that would be generate my movement of the light transceiver 312 relative to the person. The adhesive layer 318 can also reduce signal artifacts due to facial expressions.

The light-blocking layer 316 can reduce direct light coupling between the light sources 320a, 320b and the light receiver 322.

All references cited herein are hereby incorporated herein by reference in their entirety.

Having described preferred embodiments of the invention, it will now become apparent to one of ordinary skill in the art that other embodiments incorporating their concepts may be used. It is felt therefore that these embodiments should not be limited to disclosed embodiments, but rather should be limited only by the spirit and scope of the appended claims.

What is claimed is:

1. An electro-optical monitoring system comprising:
 a light transceiver comprising:
  a first light source configured to generate light having a first wavelength, the first light source coupled to receive a first periodic electrical signal having a first frequency, the first periodic electrical signal amplitude modulating the first light source to generate first amplitude modulated light, the first light source to transmit the first amplitude modulated light into biological tissue of a person at a transmission rate of at least 0.1 light transmissions per second;
  a second light source configured to generate light having a second different wavelength, the second light source coupled to receive a second periodic electrical signal having a second different frequency, the second periodic electrical signal amplitude modulating the second light source to generate second amplitude modulated light, the second light source to transmit the second amplitude modulated light into the biological tissue of the person at a rate of at least 0.1 light transmissions per second; and
  a light receiver configured to receive light from the biological tissue, the received light indicative of a combination of the first amplitude modulated light and the second amplitude modulated light having passed into and out of the biological tissue, the light receiver adapted to provide an electronic transceiver output signal indicative of at least one characteristic of the received light; and
 a processing/storage circuit, comprising:
  a first electronic signal source to generate the first periodic electrical signal;
  a second electronic signal source to generate the second periodic electrical signal;
  an amplitude demodulator configured to amplitude demodulate the transceiver output signal to provide a first demodulated signal representative of a first characteristic of the received light and to provide a second demodulated signal representative of a second different characteristic of the received light;
  a signal processor coupled to said amplitude demodulator and adapted to process the first demodulated signal and the second demodulated signal to generate a processed signal, wherein the processed signal includes signal samples having a sample rate of at least 0.1 samples per second;
  and
  a storage device coupled to said signal processor and adapted to store at least four hours of the processed signal as a stored-processed signal, wherein the stored-processed signal has a stored signal duration sufficient to detect an intermittent medical condition of the person having an occurrence period of at least four hours.

2. The electro-optical monitoring system of claim 1, wherein said light transceiver includes at least four light sources for providing at least two different light wavelengths and at least two light receivers.

3. The electro-optical monitoring system of claim 1, wherein said signal processor includes at least two of:
 a physiology measurement processor adapted to measure at least one of a heart rate, a respiration rate, a Mayer wave, a heart beat interval, a respiration interval, or a Mayer wave period of the person in response to the transceiver output signal;
 a concentration measurement processor adapted to measure a concentration of at least one of oxyhemoglobin, deoxyhemoglobin, water, cytochrome, lipid, or a fluorescent molecule of the person in response to the transceiver output signal;
 an oxygenation measurement processor adapted to measure a tissue oxygenation of the person in response to the transceiver output signal;
 a blood volume measurement processor adapted to measure a blood volume of the person in response to the transceiver output signal;

a scattering measurement processor adapted to measure a scattering characteristic of the person in response to the transceiver output signal;

a molecule property measurement processor adapted to measure the change in at least one of a concentration, a lifetime, or a quantum yield of a fluorochrome molecule;

a drug processor adapted to measure at least one of a pharmacodynamic characteristic or a pharmacokinetic characteristic of a drug;

a sudden infant death syndrome detection processor adapted to detect a drop in oxygenation level of the person in response to the transceiver output signal;

a seizure detection processor adapted to detect a seizure of the person in response to the transceiver output signal;

a vasomotor symptom detection processor adapted to detect a vasomotor symptom of the person in response to the transceiver output signal;

a dizzy spell detection processor adapted to detect a dizzy spell of the person in response to the transceiver output signal;

an ischemia detection processor adapted to detect ischemia of the person in response to the transceiver output signal;

a stroke recovery detection processor adapted to characterize a stroke recovery of the person in response to the transceiver output signal;

a hemorrhage detection processor adapted to detect a hemorrhage of the person in response to the transceiver output signal;

a heart condition detection processor adapted to detect a heart condition of the person in response to the transceiver output signal;

a hallucination episode detection processor adapted to detect characteristic brain activity associated with a hallucination of the person in response to the transceiver output signal; or a density change processor adapted to detect a density change in the biological tissue in response to the transceiver output signal.

4. The electro-optical monitoring system of claim 1, wherein said storage device comprises a data transfer/marking software module adapted to store at least one of a time tag or a detection tag with the stored processed data, wherein the time tag is stored in response to at least one of an event detection by said signal processor or a manual indication by the person, and the detection tag is stored in response to the detection by said signal processor.

5. The electro-optical monitoring system of claim 1, wherein said storage device comprises a data compression software module adapted to compress the processed signal.

6. The electro-optical monitoring system of claim 1, wherein said storage device comprises:

a recirculating buffer memory coupled to said signal processor; and a capture memory coupled to the recirculating buffer memory, wherein the contents of the recirculating buffer memory are transferred to the capture memory in response to at least one of an event detection by said signal processor or a manual indication.

7. The electro-optical monitoring system of claim 1, wherein the processing/storage circuit further comprises an event input device coupled to said storage device and adapted to receive a manual indication from the person that a symptom associated with a medical condition is occurring, wherein a time tag is stored to the stored data in response to the manual indication.

8. The electro-optical monitoring system of claim 1, wherein further comprising a reference sensor adapted to sense a characteristic of at least one of the person or said light transceiver and to provide a reference signal indicative of the characteristic, and wherein the signal processor is adapted to process the transceiver output signal and the reference signal to provide the processed signal.

9. The electro-optical monitoring system of claim 8, wherein the reference sensor comprises a motion sensor, the characteristic comprises a motion, and the reference signal comprises a motion signal.

10. The electro-optical monitoring system of claim 1, wherein said light transceiver has an adhesive surface such that said light transceiver can be directly adhesively coupled to the person.

11. The electro-optical monitoring system of claim 1, further comprising an external computing platform coupled to and apart from the light transceiver or the processing/storage circuit, which is coupled to receive at least one of the transceiver output signal, the processed signal, or the stored processed signal.

12. The electro-optical monitoring system of claim 11, wherein the external computing platform is further coupled to receive at least one of an event detection signal from said signal processor or a reference signal indicative of a characteristic of at least one of the person or said light transceiver.

13. The electro-optical monitoring system of claim 11, wherein the external computing platform includes at least two of:

a physiology measurement processor adapted to measure at least one of a heart rate, a respiration rate, a Mayer wave, a heart beat interval, a respiration interval, or a Mayer wave period of the person in response to the transceiver output signal;

a concentration measurement processor adapted to measure a concentration of at least one of oxyhemoglobin, deoxyhemoglobin, water, cytochrome, lipid, or a fluorescent molecule of the person in response to the transceiver output signal;

an oxygenation measurement processor adapted to measure a tissue oxygenation of the person in response to the transceiver output signal;

a blood volume measurement processor adapted to measure a blood volume of the person in response to the transceiver output signal;

a scattering measurement processor adapted to measure a scattering characteristic of the person in response to the transceiver output signal;

a molecule property measurement processor adapted to measure the change in at least one of a concentration, a lifetime, or a quantum yield of a fluorochrome molecule;

a drug processor adapted to measure at least one of a pharmacodynamic characteristic or a pharmacokinetic characteristic of a drug in response to the transceiver output signal;

a sudden infant death syndrome detection processor adapted to detect a drop in oxygenation level of the person in response to the transceiver output signal;

a seizure detection processor adapted to detect a seizure of the person in response to the transceiver output signal;

a vasomotor symptom detection processor adapted to detect a vasomotor symptom of the person in response to the transceiver output signal;

a dizzy spell detection processor adapted to detect a dizzy spell of the person in response to the transceiver output signal;
an ischemia detection processor adapted to detect ischemia of the person in response to the transceiver output signal;
a stroke recovery detection processor adapted to characterize a stroke recovery of the person in response to the transceiver output signal;
a hemorrhage detection processor adapted to detect a hemorrhage of the person in response to the transceiver output signal;
a heart condition detection processor adapted to detect a heart condition of the person in response to the transceiver output signal;
a hallucination episode detection processor adapted to detect characteristic brain activity associated with a hallucination of the person in response to the transceiver output signal; or
a density change processor adapted to detect a density change in the biological tissue in response to the transceiver output signal.

14. The electro-optical monitoring system of claim 1, wherein the signal processor comprises:
an artifact removal processor configured to remove an artifact from the transceiver output signal, wherein the artifact is a result of movement of facial muscles of the patient.

15. The electro-optical monitoring system of claim 1, wherein the light transceiver and the processing/storage circuit are contained in respective structures, each structure having a respective selected size, a respective selected shape, and a respective selected weight, each selected to be wearable by the person under ambulatory conditions.

16. The electro-optical monitoring system of claim 1, wherein the light transceiver comprises at least two light receivers, each light receiver adapted to provide a respective electronic transceiver output signal, wherein the processing/storage circuit comprises a plurality of amplitude demodulators, each amplitude demodulator configured to amplitude demodulate one of the transceiver output signals.

17. The electro-optical monitoring system of claim 16, wherein the light transceiver is operable to vary the amplitude of each of the amplitude modulated lights in two periodic binary amplitude states, one of the states having zero amplitude.

18. The electro-optical monitoring system of claim 1, wherein said signal processor comprises:
a concentration measurement processor adapted to measure a concentration of at least one of oxyhemoglobin, deoxyhemoglobin, water, cytochrome, lipid, or a fluorescent molecule of the person in response to the transceiver output signal.

19. The electro-optical monitoring system of claim 1, wherein said signal processor comprises:
a physiology measurement processor adapted to measure at least one of a heart rate, a respiration rate, a Mayer wave, a heart beat interval, a respiration interval, or a Mayer wave period of the person in response to the transceiver output signal.

20. The electro-optical monitoring system of claim 1, wherein the signal processor comprises a concentration measurement processor to use the first and second demodulated signals to determine a concentration of oxyhemoglobin, a concentration of deoxyhemoglobin, and a concentration of total hemoglobin, wherein the processed signal is generated in accordance with the determined concentration of oxyhemoglobin, the determined concentration of deoxyhemoglobin, and the determined concentration of total hemoglobin.

21. A method of monitoring a person under ambulatory conditions, comprising:
generating a first periodic electrical signal having a first frequency;
generating a second periodic electrical signal having a second different frequency;
amplitude modulating a first light source in response to the first periodic electrical signal to generate first amplitude modulated light, the first light source configured to generate light having a first wavelength;
modulating a second light source in response to the second periodic electrical signal to generate a second amplitude modulated light, the second light source configured to generate light having a second different wavelength;
transmitting the first amplitude modulated light into biological tissue of the person at a light transmission rate of at least 0.1 transmissions per second;
transmitting the second amplitude modulated light into the biological tissue of the person at a light transmission rate of at least 0.1 transmissions per second;
receiving light from the biological tissue, the received light indicative of a combination of the first amplitude modulated light and the second amplitude modulated light having passed into and out of the biological tissue;
generating an electronic transceiver output signal indicative of a characteristic of the received light;
amplitude demodulating the transceiver output signal to provide a first demodulated signal representative of a first characteristic of the received light and to provide a second demodulated signal representative of a second different characteristic of the received light;
processing the first demodulated signal and the second demodulated signal to provide a processed signal wherein the processed signal includes signal samples having a sample rate of at least 0.1 samples per second; and
storing at least four hours of the processed signal as a stored-processed signal, wherein the stored-processed signal has a stored signal duration sufficient to detect an intermittent medical condition of the person having an occurrence period of at least four hours.

22. The method of claim 21, wherein said light transceiver includes at least four light sources for providing at least two different light wavelengths and at least two light receivers.

23. The method of claim 21, wherein the processing includes at least two of:
measuring physiology parameter of the person in response to the transceiver output signal;
measuring a concentration of a molecule in the body of the person in response to the transceiver output signal;
measuring a tissue oxygenation of the person in response to the transceiver output signal;
measuring a blood volume of the person in response to the transceiver output signal;
measuring a scattering of a tissue of the person in response to the transceiver output signal;
measuring at least one of a concentration, a lifetime, or a quantum yield of a fluorochrome molecule in response to the transceiver output signal;
measuring at least one of a pharmacodynamic characteristic or a pharmacokinetic characteristic of a drug in response to the transceiver output signal;

detecting a sudden infant death syndrome of the person in response to the transceiver output signal;

detecting a vasomotor symptom of the person in response to the transceiver output signal;

detecting a dizzy spell of the person in response to the transceiver output signal;

detecting an ischemia of the person in response to the transceiver output signal;

characterizing a stroke recovery of the person in response to the transceiver output signal;

detecting a hemorrhage of the person in response to the transceiver output signal;

detecting a heart condition of the person in response to the transceiver output signal;

detecting a hallucinogenic episode of the person in response to the transceiver output signal; or detecting a density change in the biological tissue in response to the transceiver output signal.

24. The method of claim 21, wherein said storage device comprises a data transfer/marking software module adapted to store at least one of a time tag or a detection tag to the stored processed data, wherein the time tag is stored in response to at least one of an event detection by said signal processor or a manual indication, and the detection tag is stored in response to the detection by said signal processor.

25. The method of claim 21, wherein said storage device comprises a data compression software module adapted to compress the processed signal.

26. The method of claim 21, wherein the storing comprises:
storing the processed signal in a recirculating buffer memory; and
transferring contents of the recirculating buffer memory to a capture memory, wherein the contents of the recirculating buffer memory are transferred to the capture memory in response to at least one of an event detection by said signal processor or a manual indication.

27. The method of claim 21, further comprising receiving a manual indication from the person that a symptom associated with a medical condition is occurring, wherein a time tag is stored to the stored data in response to the manual indication.

28. The method of claim 21, further comprising:
sensing a characteristic of at least one of the person or said light transceiver to provide a reference signal indicative of the characteristic; and
processing the transceiver output signal and the reference signal to provide the processed signal.

29. The method of claim 28, wherein the characteristic comprises a motion and the reference signal comprises a motion signal.

30. The method of claim 21, wherein the transmitting light and the receiving light include adhesively coupling a light transceiver to the person.

31. The method of claim 21, wherein the method further comprises:
receiving at least one of the transceiver output signal, the processed signal, or the stored processed signal with an external computing platform; and
processing that least one of the transceiver output signal, the processed signal, or the stored processed signal with the external computing platform.

32. The method of claim 31, wherein the processing with the external computing platform includes at least two of:

measuring physiology parameter of the person in response to the transceiver output signal;

measuring a concentration of a molecule in the body of the person in response to the transceiver output signal;

measuring a tissue oxygenation of the person in response to the transceiver output signal;

measuring a blood volume of the person in response to the transceiver output signal;

measuring a scattering of a tissue of the person in response to the transceiver output signal;

measuring at least one of a concentration, a lifetime, or a quantum yield of a fluorochrome molecule in response to the transceiver output signal;

measuring at least one of a pharmacodynamic characteristic or a pharmacokinetic characteristic of a drug in response to the transceiver output signal;

detecting a sudden infant death syndrome of the person in response to the transceiver output signal;

detecting a vasomotor symptom of the person in response to the transceiver output signal;

detecting a dizzy spell of the person in response to the transceiver output signal;

detecting an ischemia of the person in response to the transceiver output signal;

characterizing a stroke recovery of the person in response to the transceiver output signal;

detecting a hemorrhage of the person in response to the transceiver output signal;

detecting a heart condition of the person in response to the transceiver output signal;

detecting a hallucinogenic episode of the person in response to the transceiver output signal; or detecting a density change in the biological tissue in response to the transceiver output signal.

33. The method of claim 21, wherein the processing comprises:
removing an artifact from the transceiver output signal, wherein the artifact is a result of movement of facial muscles of the patient.

34. The method of claim 21, wherein the amplitude modulated light comprises two periodic binary amplitude states, one of the states having zero amplitude.

35. The method of claim 21, wherein the processing comprises:
measuring a concentration of at least one of oxyhemoglobin, deoxyhemoglobin, water, cytochrome, lipid, or a fluorescent molecule of the person in response to the transceiver output signal.

36. The method of claim 21, wherein the processing comprises:
measuring physiology parameter of the person in response to the transceiver output signal, wherein the physiology parameter comprises at least one of a heart rate, a respiration rate, a Mayer wave, a heart beat interval, a respiration interval, or a Mayer wave period of the person in response to the transceiver output signal.

37. The method of claim 21, wherein the processing comprises determining, from the first and second demodulated signals, a concentration of oxyhemoglobin, a concentration of deoxyhemoglobin, and a concentration of total hemoglobin, wherein the processed signal is generated in accordance with the determined concentration of oxyhemoglobin, the determined concentration of deoxyhemoglobin, and the determined concentration of total hemoglobin.

* * * * *